(12) United States Patent
Hardy

(10) Patent No.: US 6,423,544 B1
(45) Date of Patent: Jul. 23, 2002

(54) COMPOSITIONS AND METHODS FOR PRODUCING RECOMBINANT VIRIONS

(75) Inventor: Stephen F. Hardy, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/608,730

(22) Filed: Jun. 30, 2000

Related U.S. Application Data

(63) Continuation-in-part of application No. 09/476,299, filed on Dec. 30, 1999, now Pat. No. 6,242,259.
(60) Provisional application No. 60/114,732, filed on Dec. 31, 1998.

(51) Int. Cl.[7] .................. C12N 15/86; C12N 15/63; C12N 5/10; C07H 21/04
(52) U.S. Cl. .................. 435/456; 435/320.1; 435/457; 435/325; 536/23.1; 536/23.72
(58) Field of Search .................. 536/23.1, 23.72; 435/320.1, 325, 456, 455, 457

(56) References Cited

FOREIGN PATENT DOCUMENTS

| WO | WO 96/37616 | 11/1996 |
| WO | WO 97/38087 | 10/1997 |

OTHER PUBLICATIONS

Dubensky et al., "Sindbis Virus DNA–Based Expression Vectors: Utility for in Vitro and in Vivo Gene Transfer" *J. Virology* 70(1):508–519, Jan., 1996.
Pushko et al., "Replicon–Helper Systems from Attenuated Venezuelan Equine Encephalitis Virus: Expression of Heterologous Genes in Vitro and Immunization Against Heterologous Pathogens in Vivo" *Virology* 239:389–401, 1997.
Frolov et al., "Sindbis Virus Replicons and Sindbis Virus: Assembly of Chimeras and of Particles Deficient in Virus RNA" *J. Virology* 71(4):2819–2829, Apr., 1997.
Frolov et al., "Alphavirus–Based Expression Vectors: Strategies and Applications" *Proc. Natl. Acad. Sci. USA* 93:11371–11377, Oct., 1996.
Polo et al., "Stable Alphavirus Packaging Cell Lines for Sindbis Virus–and Semiliki Forest Virus–Derived Vectors" *Proc. Natl. Acad. Sci. USA* 96:4598–4603, Apr., 1999.
Semerdou and Liljestrom, "Two–Helper RNA System for Production of Recombinant Semliki Forest Virus Particles" *J. Virology* 73(2):1092–1098, Feb., 1999.
Bredenbeek et al., "Sindbis Virus Expression Vectors: Packaging of RNA Replicons by Using Defective Helpter RNAs" *J. Virology* 67(11):5439–6446, Nov., 1993.
Berglund et al., "Alphaviruses as Vectors for Gene Delivery" *TIBTECH* 14: 130–134, Apr., 1996.
Krug et al., "Enzymatic Synthesis of a 21–Nucleotide Coat Protein Binding Fragment of R17 Ribonucleic Acid," *Biochemistry* 21:4713–4720 (1982).
Schneider et al., "Selection of High Affinity RNA Ligands to the Bacteriophage R17 Coat Protein," *J. Mol. Biol.* 228:862–869 (1992).
Stripecke et al., "Proteins Binding to 5' Untranslated Region Sites: a General Mechanism for Translational Regulation of mRNAs in Human and Yeast Cells," *Mol. Cell. Biol.* 14(9):5898–5909 (1994).
Stripecke and Hentze, "Bacteriophage and Spliceosomal Proteins Function as Position–Deptendent Cis/Trans Repessors of mRNA Translation in vitro," *Nuc. Acids Res.* 20(21):5555–5564 (1992).
Werstuck and Green, "Controlling Gene Expression in Living Cells Through Small Molecule–RNA Interactions," *Science* 282:296–298 (1998).

*Primary Examiner*—Robert A. Schwartzman
*Assistant Examiner*—Katharine F Davis
(74) *Attorney, Agent, or Firm*—Robert P. Blackburn; Anne S. Dollard; Dahna S. Pasternak

(57) ABSTRACT

The invention provides host cells comprising a translation operator sequence (TOP) and packaging elements. Also provided are viral vectors comprising a TOP operably linked to a transgene. Also provided are methods of using these host cells and viral vectors to produce recombinant virions.

33 Claims, 14 Drawing Sheets

Sequences for Binding of R17 Ligand

MS2 operator     5TOP     TOP

Sequences for Binding of R17 Ligand

```
                    U  C         A
              U C   A          C-G
         A        C-G          C-G
     A  C-G       C-G    A   A-C-G
    C-G  C-G   A-C-G         A U-A
    C-G  G-C     G-C           G-C
  A-C-G  A-U     A-U           A-U
    G-C  C-G     C-G           U-A
    C-G  C-G     C-G             A
A₁₁ A₁₄  AUAGU
U₁₂U₁₃
    G₁₀-C₁₅
    G₉ -C₁₆
  A₈G₇ -C₁₇
    U₆ -A₁₈
    A₅ -U₁₉
    C₄ -G₂₀
      A₃-U₂₁
    A₁A₂

MS2 operator   5TOP         TOP
```

FIG. 1

———— untransfected
■■■■ normal
------ + coat protein

·········· uninfected
− − − cpp
——— cre8 rAAV vector with Top sequence.

COMPOSITIONS AND METHODS FOR PRODUCING RECOMBINANT VIRIONS

CROSS-REFERENCE TO RELATED APPLICATIONS

This application is a continuation-in-part of U.S. Ser. No. 09/476,299, filed Dec. 30, 1999, now U.S. Pat. No. 6,242, 259, from which priority is claimed under 35 USC §120, which in turn is related to U.S. Provisional Application No. 60/114,732 filed Dec. 31, 1998, from which priority is claimed under 35 USC §119(e)(1), both of which applications are incorporated by reference herein in their entireties.

TECHNICAL FIELD

The present invention relates generally to recombinant DNA technology; and more specifically, to methods of producing recombinant virions. In particular, by suppressing translation of a transgene during production of recombinant virions, the methods expand the number of transgenes that can be produced as recombinant virions.

BACKGROUND

Viral vectors capable of transferring genetic material into mammalian cells have the potential to provide a wide range of experimental and therapeutic uses. See, e.g., Jolly, *Cancer Gene Therapy* 1(1):51–64, 1994); U.S. Pat. Nos. 5,399,346, 5,580,859, 5,589,466. Viral vectors can be derived from a variety of viruses, including adenoviruses, retroviruses, and alphaviruses such as Sindbis (see, e.g., Strauss and Strauss, 1994, *Microbio. Rev.*, 58:491–562). For a description of viral vectors and their uses, see, for example, *Gene Therapy: Principles and Applications* (T. Blankenstein, et., 1999, Springer-Verlag, Inc.) and *Understanding Gene Therapy* (N. Lemoine, ed., 2000, R-G Vile).

In each of these viral vector systems, it is desirable to have high levels of transgene expression in target cells. However, transgene expression during virion production is not necessary, and, in many cases, interferes with viral growth. To circumvent this problem, several groups have attempted to regulate transcription of the transgene during production of adenoviral virions, for instance by operably linking the transgene to an inducible promoter. The promoter is kept inactivated during virion production and induced in the target cell. However, this transcriptional regulation imposes many constraints on experiments and therapies.

Thus, there remains a need for methods of suppressing transgene expression during virion production while maintaining high transgene expression in the target cell(s).

SUMMARY OF THE INVENTION

The present invention solves this and other problems by providing systems wherein expression of the heterologous transgene may be reduced (suppressed) in desired cells, including during the virion packaging process. The methods allow for the suppression of transgene translation in virion producing cells while maintaining the capacity for high level expression and translation of the transgene in all other cell types. The system described is applicable to a variety of viral vectors and, in addition, can be combined with other virion production systems, including, for example, adenovirus virion construction in a cre-lox system.

In one aspect the invention includes a host cell (e.g., a 293 cell) comprising a TOP-binding ligand and packaging elements. In certain embodiments, the TOP-binding ligand and/or one or more packaging elements is encoded by one or more polynucleotides while in other embodiments, the TOP-binding ligand and/or one or more of the packaging elements are introduced into the host cell via other means, such as injection or the like. Thus, introduction of polynucleotides encoding the desired gene product can be used in combination with other means of introducing molecules into the host cell. In certain embodiments, the host cell is stably or transiently transfected with a nucleic acid molecule encoding the TOP-binding ligand (e.g., an MS2 or R17 coat protein) and stably or transiently transfected with the polynucleotides encoding the packaging elements (e.g, E1A and E1B). In yet other embodiments, the host cell further comprises a cre recombinase.

In another aspect, the invention includes a method of producing recombinant virions comprising culturing a recombinant viral vector comprising a translational operator sequence (TOP) operably linked to a transgene with (i) a TOP-binding ligand and (ii) packaging elements; under conditions such that expression of the transgene is suppressed during production of the virions. In certain embodiments, the recombinant viral vector is an adenovirus vector, a retroviral (e.g., lentiviral vector such as FIV, HIV, HIV-1, HIV-2 and SIV), an alphaviral vector or an adeno-associated vector. The TOP-binding ligand can be, for example, an MS2 coat protein or an R17 coat protein. The TOP-binding ligand and/or the packaging elements may be encoded by a polynucleotide that is stably or transiently transfected into a host cell, for example a 293 cell that expresses an MS2 coat protein, an E1A protein and an E1B protein. In certain embodiments, any of the recombinant viral vectors described herein further comprise an mRNA 5',5',7-methyl guanosine triphosphate cap sequence ($^{m7}$G-cap) and the TOP is located within about 60 base pairs or within about 30 base pairs of the mRNA $^{m7}$G-cap sequence. In embodiments where the recombinant viral vector is derived from adenovirus, the recombinant adenoviral vector and the packaging elements can be cultured the presence of an E1, E3 deleted adenovirus construct having loxP sites flanking the packaging site and a cre recombinase.

In yet another aspect, the invention includes a viral vector (e.g., derived from an adenovirus, an alphavirus, a retrovirus such as a lentivirus, or an adeno-associated virus) comprising a transgene operably linked to a TOP sequence. In certain embodiments, the TOP sequence is derived from an MS2 or R17 bacteriophage.

These and other embodiments of the present invention will readily occur to those of ordinary skill in the art in view of the disclosure herein.

BRIEF DESCRIPTION OF THE FIGURES

FIG. 1 is an illustration of sequence modifications (SEQ ID NOs: 1, 2, 3) to an alphavirus vector that allow for binding of a bacteriophage protein.

FIG. 7C depicts the results of two separate experiments.

FIG. 9A depict vectors having the retrovirus LTR promoter to express the transgene. U3, R and U5 are segments of retrovirus LTR's. FIG. 9B depicts a Sin vector where the 3' LTR contains a deletion in U3. If the vector is a lentivirus vector the 3' LTR may or may not contain a deletion in the U3 sequence.

DETAILED DESCRIPTION OF THE INVENTION

Figure 2:
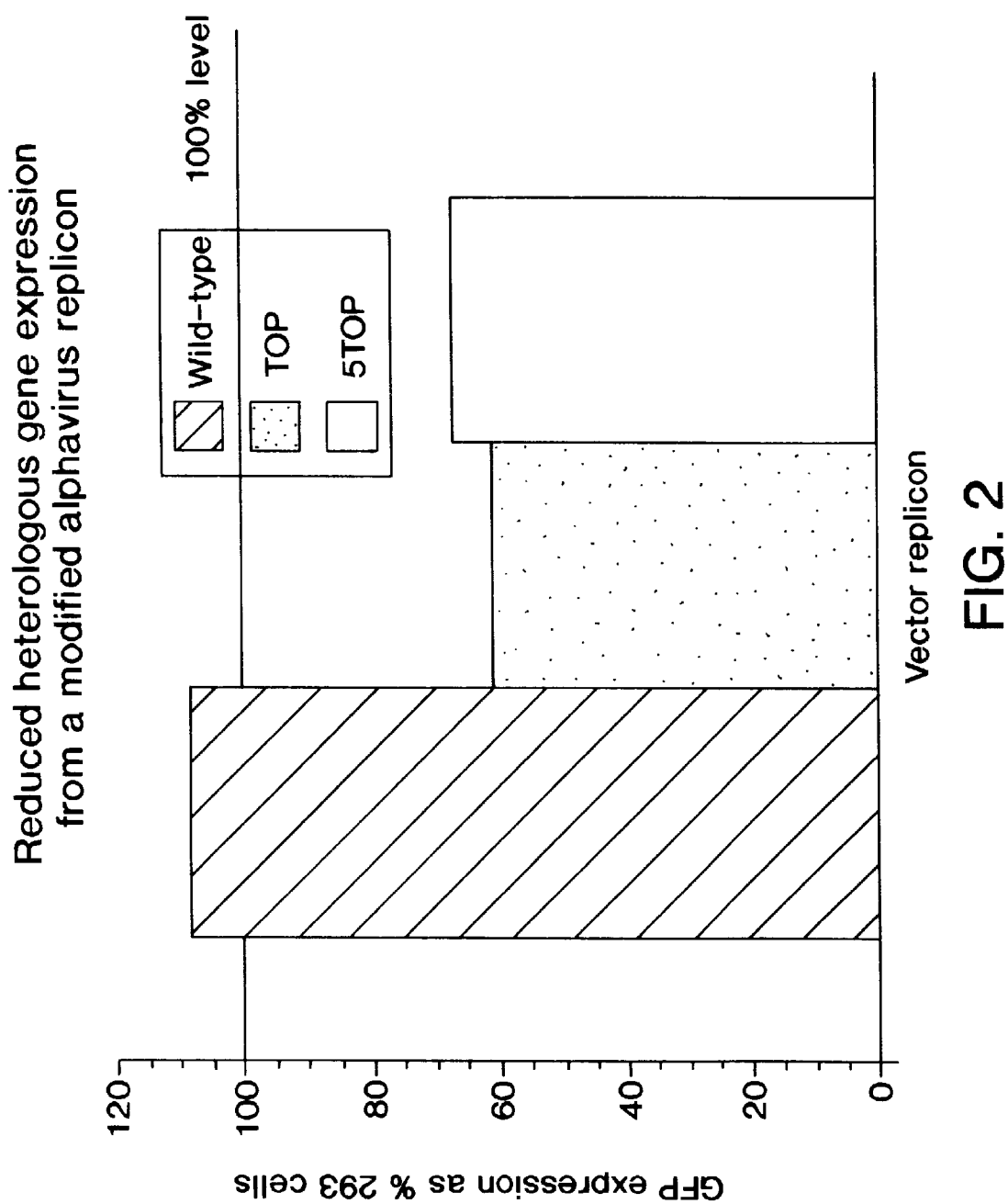
FIG. 2 is a graph demonstrating reduced expression of a heterologous transgene by an RNA binding protein specific for the sequence modifications in FIG. 1 in alphavirus.

The practice of the present invention will employ, unless otherwise indicated, conventional methods of chemistry, biochemistry, molecular biology, virology, immunology and pharmacology, within the skill of the art. Such techniques are explained fully in the literature. See, e.g., *Remington's Pharmaceutical Sciences*, 18th Edition (Easton, Penn.: Mack Publishing Company, 1990); *Methods In Enzymology* (S. Colowick and N. Kaplan, eds., Academic Press, Inc.); and Handbook of experimental *Immunology*, Vols. I–IV (D. M. Weir and C. C. Blackwell, eds., 1986, Blackwell Scientific Publications); Sambrook, et al., *Molecular Cloning: A Laboratory Manual* (2nd Edition, 1989); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); PCR (Introduction to Biotechniques Series), 2nd ed. (Newton & Graham eds., 1997, Springer Verlag).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

1. Definitions

In describing the present invention, the following terms will be employed, and are intended to be defined as indicated below.

A "translational operator," or "TOP" should be understood to refer to a nucleotide sequence that is one member of a ligand binding pair that reduces or prevents translation of mRNA (e.g., mRNA derived from a transgene) in the presence of a ligand. The TOP is typically found in the translation-initiation region (TIR) of the mRNA and may include a stem-loop structure which is believed to be involved in binding. "Aptamers" refer to single-stranded oligonucleotides (DNA or RNA) that have been artificially evolved and selected to bind tightly and specifically to target molecules such as proteins. Thus, as used herein, aptamers refer to TOPs that have been modified as compared to wild-type or TOPs that have been synthetically prepared. Preferably, the TOP sequence is not derived from the same species as the viral vector. Further, a TOP sequence by itself permits translation of the operatively linked gene. A "TOP binding ligand" or "ligand" refers to any protein or small molecule that binds to a TOP sequence. Thus, a TOP binding ligand is the second half of the ligand binding pair. The TOP ligand by association with the TOP prevents translation of the linked gene. TOP ligands include, but are not limited to, RNA binding proteins such as R17 and MS2 coat protein. Since TOP's can be created synthetically to bind at high affinity to many types of molecules, TOP ligands can include pharmaceutically acceptable molecules that bind to TOP sequences. Accordingly, it is to be understood that TOP-binding ligands can be used in a variety of forms, for instance they can be introduced into a host cell using a nucleic acid molecule which encodes a TOP-binding protein, as a protein or as other molecule.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA. For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

A "gene" refers to a polynucleotide containing at least one open reading frame that is capable of encoding a particular polypeptide or protein after being transcribed or translated. Any of the polynucleotide sequences described herein may be used to identify larger fragments or full-length coding sequences of the genes with which they are associated. Methods of isolating larger fragment sequences are known to those of skill in the art.

"Operably linked" refers to an arrangement of elements wherein the components so described are configured so as to perform their usual function. Thus, a translation operator sequence (TOP) operably linked to a transgene is capable of effecting translation of the transgene when the appropriate TOP-binding ligand (e.g., protein(s)) is present. As described above, the TOP need not be contiguous with the transgene sequence, so long as it functions to suppress translation thereof. Similarly, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the TOP or promoter sequence and the coding sequence, and the TOP or promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of molecules with which it is associated in nature (e.g., control elements or even the chromosome); and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482–489 (1981). This algorithm can be extended to use with peptide sequences using the scoring matrix developed by Dayhoff, Atlas of Protein Sequences and Structure, M. O. Dayhoff ed., 5 suppl. 3:353–358, National Biomedical Research Foundation, Washington, D.C., USA, and normalized by Gribskov, Nucl. Acids Res. 14(6):6745–6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: NCBI website.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10–12 nucleotides and up to 5000 nucleotides, and even more preferably 15–20 nucleotides, up to the number of nucleotides present in the full-length sequences described herein (e.g., see the Sequence Listing and claims), including all integer values falling within the above-described ranges.

A first polynucleotide is "derived from" a second polynucleotide if it has the same or substantially the same basepair sequence as a region of the second polynucleotide, its cDNA, complements thereof, or if it displays sequence identity as described above. Similarly, a first polypeptide is "derived from" a second polypeptide if it is (i) encoded by a first polynucleotide derived from a second polynucleotide, or (ii) displays sequence identity to the second polypeptides as described above.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified" or "isolated" when referring to a polynucleotide refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"vector construct", "viral vector," and "recombinant viral vector" refer to a nucleic acid construct which carries, and within certain embodiments of the invention, is capable of directing the expression of a sequence(s) or gene(s) of interest (e.g., transgene). A wide variety of heterologous sequences (e.g., "transgene") may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence).

"Expression cassette" refers to an assembly which is capable of directing the expression of the sequence(s) or gene(s) of interest. The expression cassette must include a promoter or promoter/enhancer which, when transcribed, is operably linked to the sequence(s) or gene(s) of interest, as well as a polyadenylation sequence. Within certain embodiments of the invention, the expression cassette described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "virion," or "recombinant virion" is defined herein as an infectious, replication-defective virus composed of a protein shell, encapsidating a heterologous nucleotide sequence of interest. Virions are produced in a suitable host cell which has had the necessary accessory functions introduced therein. In this manner, recombinant virions suitable for experimental and therapeutic uses are produced.

The term "host cell" denotes, for example, microorganisms, yeast cells, insect cells, and mammalian cells, that can be, or have been, used as recipients of a vector constructs or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

A "selectable marker" or "reporter marker" refers to a nucleotide sequence included in a gene transfer vector that has no therapeutic activity, but rather is included to allow for simpler preparation, manufacturing, characterization or testing of the gene transfer vector.

"Packaging cell" refers to a cell (or cell line) which contains those elements necessary for production of infectious recombinant virus. Such packaging cells may contain one or more expression cassettes which are capable of expressing suitable proteins or may be stably transfected with nucleic acids encoding the necessary proteins. "Packaging elements" refers to elements (e.g., proteins) necessary for the production of infectious recombinant virus.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. Non-limiting examples of cell lines useful in the practice of the present invention include 293, HeLa, CV1 and KB cells.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

As used herein, "treatment" refers to any of (i) the prevention of disease, infection or reinfection, as in a traditional vaccine, (ii) the reduction or elimination of symptoms and/or and (iii) the substantial or complete elimination of the disease or the pathogen in question. Treatment may be effected prophylactically (prior to the onset of disease or infection) or therapeutically (following the onset of disease or infection). An "effective amount" is an amount sufficient to effect beneficial or desired results. An effective amount can be administered in one or more administrations, applications or dosages.

By "nucleic acid immunization" is meant the introduction of a nucleic acid molecule encoding one or more selected transgenes (e.g., antigens) into a host cell, for the in vivo expression of the transgene (e.g., antigen, antigens, an epitope, or epitopes). The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the transgene (e.g. antigen) encoded by the nucleic acid molecule.

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2. General Overview

The present invention provides a system for suppressing the expression of transgene during production of recombinant virions, thereby expanding the number of transgenes that can be produced as recombinant virions. To this end, the invention includes methods of inhibiting translation of a viral vector transgene by operably linking a translation operator (TOP) sequence to one or more transgenes (genes of interest). Translation of the transgene is inhibited when the virions are produced in the presence of a TOP-binding ligand but, in the presence of the factors required for packaging, virion production is not affected and, indeed, may be increased and/or more stable in comparison to previous methods. In certain embodiments, the TOP sequence is used in combination with other virion production techniques, for instance the conditional cre/lox system used to produce adenovirus vectors. Thus, the invention creates a flexible system for building recombinant virions independent of the transgene activity.

3. Translation Operators (TOP) and Ligands

Central to the present invention is the inclusion of at least one translation operator sequence (TOP) to reduce expression of a heterologous transgene by suppressing translation. In preferred embodiments, the level of heterologous transgene expression during vector production is reduced at least 25%, 50%, 75%, 95%, or, 3-fold, 5-fold, 10-fold, or even about 100-fold, or any integer up to 100-fold or more, as compared to the level of expression in a target cell.

Figure 3:
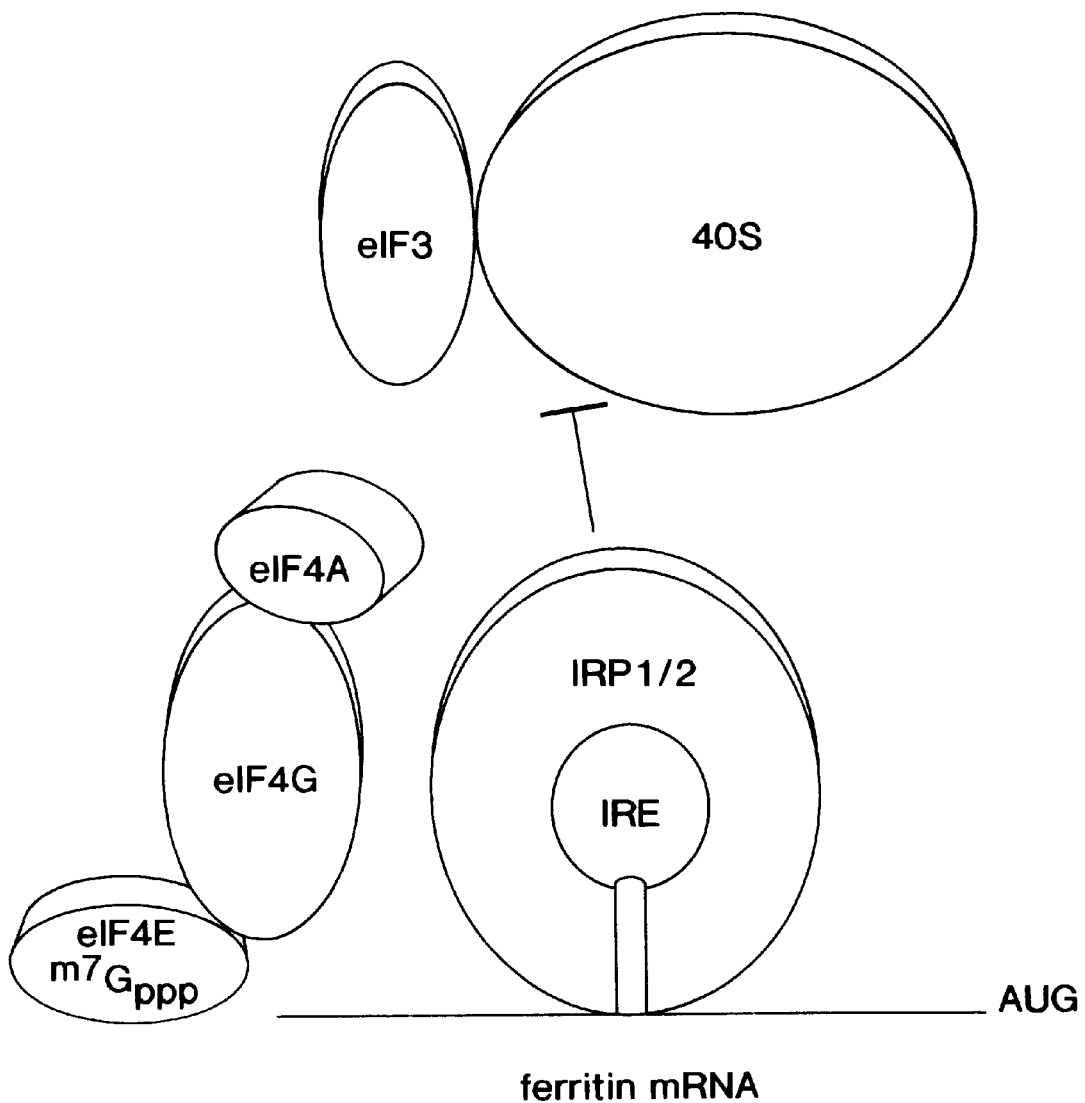
FIG. 3 is a schematic depicting blocking of translation of ferritin mRNA. IPR1/2 is shown bound to the IRE TOP and this complex is believed to sterically inhibit binding of the e1F4E/e1F4G/e1F4A protein complex which is involved in translation.

As depicted in FIG. 3, studies have shown that translation suppression plays a role in iron homeostasis in animals where translation of ferritin mRNA is blocked by iron regulatory protein (IRP) binding to the iron responsive element (IRE) near the 5' end of the mRNA. IRP mediated suppression works most effectively if the IRE is less than 60 bases from the mRNA cap. Thus, it is possible that the IRP could sterically inhibit the formation of the eIF4F complex, thereby interfering with the first step in the complex formation, eIF4E binding to the $^{m7}$GTP mRNA cap. However, recent studies have yielded a more complex picture in that the formation of eIF4F is not inhibited by bound IRP, but instead subsequent binding between the eIF3/40S ribosome complex and eIF4F is blocked. See, e.g., Muckenthaler et al. (1998) *Molecular Cell* 2:383–388; Sachs et al. (1997) *Cell* 89:831–838.

Translation suppression is also a key host cell defense against viral infections including adenoviruses. One step in this process is dephosphorylation of eIF4E late in the adenoviral life cycle. Phosphorylated eIF4E is the limiting translation factor whose activity regulates the global translation level. Adenoviral late genes circumvent the need for eIF4E through a shared 5' untranslated region called the tripartite leader that enables late mRNA's to be translated without eIF4E. The result is a decline in host gene translation, while late viral genes are being made.

It has also been reported that the MS2 coat protein and its RNA binding site can substitute for the IRP and IRE, blocking translation both in vitro and in vivo (see, e.g., Stripecke and Hentze (1992) *Nuc. Acids Res.* 20(21):5555–5564; Stripecke et al. (1994) *Mol. Cell. Biol.* 14(9):5898–5909; Muckenthaler et al., supra and Sachs et al., supra). MS2 coat protein binding to the translation operator (TOP) has been extensively studied, yielding a detailed understanding of the bases and secondary structure critical to binding, and a high resolution structure of coat protein-RNA complexes.

Thus, a translation operator (TOP) refers to any nucleotide sequence which is capable of binding to a ligand, for example a nucleotide sequence that is a binding site for an RNA binding protein, such as, for example an R17 or MS2 coat binding protein. The MS2 translation operator overlaps the bacterial ribosome binding site and AUG for the replicase protein so that both are shielded by coat protein bound to the RNA, thereby preventing translation of the replicase protein. The RNA sequence for the MS2 phage translation operator is: ACAGAGGAUUACCCAUGU (SEQ ID NO:4). Similarly, the RNA binding site for bacteriophage R17 coat protein (Krug et al. (1982) *Biochemistry* 21:4713–4720) can also be used. The minimal R17 binding site comprises a sequence AAACAUGAGGAUUAC-CCAUGU (SEQ ID NO:1) and forms a stem loop structure that appears to be absolutely required for binding. Analysis of a population of high affinity RNA ligands to the coat protein revealed the components of a hairpin that promote favorable interactions with the coat protein (Schneider et al. 1992 *J. Mol. Biol.* 228:862–869). As described below in the Examples and in FIGS. 1 and 4, the TOP sequence may contain one or more base changes, so long as overall high affinity binding structure is preserved. (See, also, Loward et al. (1987) *Nucleic Acids Research* 15:10483–10493). In certain instances, an artificially generated TOP may be referred to as an "aptamer".

Non-limiting examples of suitable ligands which bind to the TOP include, the coat proteins from R17 or MS2 bacteriophage (see, NCBI Accession Numbers VCBPM2 and VCBPR7 respectively); antibiotics such as tobramycin, and Hoechst dyes such as H33258 or H33342. In certain embodiments, the ligand (e.g., coat protein) is expressed by the packaging cell line (see, e.g., U.S. Pat. No. 5,789,245), for example by stably transfecting the appropriate cell line.

In preferred embodiments, the TOP sequence is positioned near or adjacent the binding site of the protein(s)

responsible for initiating translation of mRNA. For example, in adenovirus production where binding of the eIF4E protein complex to the 5',5',7-methyl guanosine triphosphate cap site ($^{m7}$G-cap) is believed to initiate translation, the TOP sequence would be positioned near the $^{m7}$G cap site. Preferably, the TOP sequence is positioned within about 1 to 60 bases (including all integer values in this range) after the binding site (e.g., $^{m7}$G cap), more preferably between about 1 to 30, even more preferably between about 1 to 15 and even more preferably immediately adjacent to the binding site.

4. Viral Vectors

The present invention provides methods for improving the variety of recombinant virions that can be produced including, but not limited to, adenoviral-, alphaviral-, adeno-associated-, and retroviral-based virions. For a description of these and other viral vectors useful in the practice of the present invention, see, for example, *Gene Therapy: Principles and Applications* (T. Blankenstein, et., 1999, Springer-Verlag, Inc.) and *Understanding Gene Therapy* (N. Lemoine, ed., 2000, R-G Vile). Using the methods described herein, stability and/or yield of recombinant virions is preferably increased at least 2-fold as compared to methods which do not involve TOP, more preferably between about 2 and 10 fold, more preferably between about 10 and 100 fold, and even more preferably 100 fold or greater.

4.A. Adenovirus Vectors

Adenoviral vectors have been described for use in gene delivery. Unlike retroviruses which integrate into the host genome, adenoviruses persist extrachromosomally thus minimizing the risks associated with insertional mutagenesis (See, e.g., Haj-Ahmad and Graham, *J. Virol.* (1986) 57:267–274; Bett et al., *J. Virol.* (1993) 67:5911–5921; Mittereder et al., *Human Gene Therapy* (1994) 5:717–729; Seth et al., *J. Virol.* (1994) 68:933–940; Barr et al., *Gene Therapy* (1994) 1:51–58; Berkner, K. L. *BioTechniques* (1988) 6:616–629; and Rich et al., *Human Gene Therapy* (1993) 4:461–476). The E1A and E3 regions are typically deleted from the majority of recombinant adenoviral vectors. The E1A region is the first region to be transcribed upon nuclear entry and is essential for viral replication. The E3 region appears not be required for viral growth in culture and has also been shown to play a key role in pathogenesis. Accordingly, mature (e.g., packaged) recombinant adenovirus virions are produced by culturing the recombinant adenovirus vector carrying the transgene with a cell line (e.g., a 293 human kidney cell line) that has been stably transfected with the E1A and E1B region of the adenoviral genome.

In one embodiment of the present invention, expression of the transgene is suppressed during virion production by operably linking a TOP to the transgene. In the presence of a TOP-binding ligand, translation of the transgene is suppressed. However, in the presence of other necessary factors for virion production (e.g., packaging factors), virions are still produced. It will be apparent to those skilled in the art from the teachings herein that the virion packaging factors can be provided in cis, in trans or combinations thereof. For example, a packaging cell line can be transiently or stably transfected with one or more expression cassettes which direct expression of a TOP-binding ligand and the proteins required for packaging adenovirus vectors (e.g., E1A proteins) into virions.

In other embodiments of the present invention, adenoviral virions are produced using methods of transgene translation suppression as described above in combination with a cre-lox system of adenoviral vector assembly as described in Hardy et al. (1997) *J. Virol.* 71:1842–1849. The cre-lox system makes use of a special Ψ5 adenovirus in which the packaging site is flanked by loxP sites. Thus, in certain embodiments of the present invention, a shuttle plasmid carrying the TOP sequence and a donor Ψ5 adenovirus construct are assembled using a cell line that expresses both cre recombinase (Sauer (1987) *Mol. Cell Biol.* 7:2087–2096) and a TOP binding ligand. As described below, a novel cell line, termed CPP, was generated to express cre recombinase, an MS2 coat protein and E1 proteins. Other appropriate host cell lines could be prepared using the methods described in the present specification, for example by stably transfected 293 cells with one or more expression cassettes encoding a TOP-binding ligand and appropriate packaging factors.

The presence of cre recombinase allows recombination between the donor virus Ψ5 and the shuttle plasmid to produce a new adenovirus virion. Further, the presence of an appropriate TOP binding ligand suppresses translation of the transgene during production of the virions. Exemplified below is adenovirus virion production using the following components: a shuttle plasmid containing the CMV immediate/early promoter and a translational operator sequence (TOP), for example from MS2 bacteriophage, a 293 cell line expressing MS2 coat protein plus cre recombinase, and an E1, E3 deleted donor adenovirus with loxP sites flanking the packaging site. Transgene expression is suppressed during virion manufacturing but it is made constitutively when the virion infects target cells. As noted above, virtually any RNA-binding protein can be used to bind to the TOP.

4.B. Alphavirus Vectors

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention. For a description of Sindbis-virus derived vectors useful for the practice of the instant methods, see, Dubensky et al., *J. Virol.* (996) 70:508–519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

The general strategy for construction of alphaviral-based expression vectors has been to substitute some or all of the viral structural protein genes with a heterologous gene, maintaining transcriptional control via the highly active subgenomic RNA promoter. Vectors of this configuration are termed RNA "replicons" and may be transcribed in vitro from cDNA using a bacteriophage promoter, or, generated in vivo directly from DNA when linked to a eukaryotic promoter. Currently, alphavirus replicon RNA is packaged into recombinant virions by transient co-transfection with in vitro transcribed defective helper RNA, or, using stable packaging cell lines having structural protein expression cassettes. The structural protein expression cassette(s) used for vector packaging encode either the intact "native" alphavirus structural polyprotein that is post-translationally processed into mature C, E2, and E1; or, alphavirus structural proteins that have been split into separate cassettes encoding either C or E2/E1.

Provided by the present invention are methods to reduce expression of a heterologous sequence (also referred to as a "transgene") from an alphavirus vector during the production of recombinant alphavirus virions. As with other viral vectors such as adenovirus, these methods are advantageous for alphavirus because of the high level expression of transgene in cells during vector packaging and the often deleterious effects of transgene expression on final virion particle titer due to interference with glycoprotein transport and processing, competition with alphavirus gene product function, and general toxicity for the host or packaging cell.

The approaches provided herein to reduce expression of a transgene in alphavirus vectors are directed at the reduction of transcription or translation of the vector subgenomic RNA. Such approaches are deemed necessary because reduction in the overall ability of the vector itself to replicate would have an adverse effect of the production of alphavirus virions.

Figure 8:
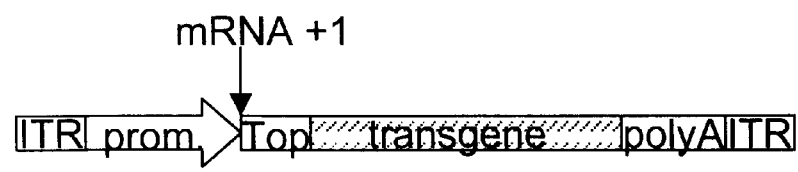
FIG. 8 is a schematic depicting one example of a rAAV vector where "ITR" represents inverted terminal repeat; "prom" represents shows the promoter position; "Top" shows the location for TOP sequences; and "PolyA" represents the poly adenylation sequence.

Thus, in certain embodiments, methods of producing alphavirus virions are provided, comprising introducing into a population of cells an alphavirus vector construct (e.g., vector RNA replicon) and one or more expression cassettes encoding TOP-binding ligands and proteins capable of packaging mature alphavirus virions (e.g., an expression cassette encoding capsid and glycoprotein E2 and an expression cassette encoding capsid and glycoprotein E1), such that recombinant alphavirus virions are produced, wherein the alphavirus vector construct or vector RNA replicon further comprises a TOP (e.g., an RNA aptamer sequence) that binds to a ligand provided, therein reducing translation from the subgenomic RNA. Preferably, the TOP is inserted within the vector sequence corresponding to said subgenomic RNA.

As specifically noted above, any TOP (e.g., RNA aptamer) with a known binding ligand may be readily substituted by one of skill in the are, using this disclosure. In utilizing an RNA aptamer and ligand binding pair, it is preferable to choose an aptamer and site for insertion into the vector that does not interfere with replication of the alphavirus vector or with translation of the subgenomic mRNA in the absence of its ligand. In preferred embodiments, the TOP within the alphavirus vector construct or vector RNA replicon binds to a ligand that is an antibiotic, such as Tobramycin or Kanamycin. In another preferred embodiment, the RNA aptamer within the alphavirus vector construct or vector RNA replicon binds to Hoechst dyes H33258 or H33342 (Werstuck and Green, 1998, *Science* 282:296–298). In particularly preferred embodiments, the RNA aptamer is inserted within the 5'-nontranslated region of the alphavirus subgenomic RNA.

4.C. Retroviral Vectors

Retroviruses are diploid positive-strand RNA viruses that replicate through an integrated DNA intermediate. In particular, upon infection by the RNA virus, the retroviral genome is reverse-transcribed into DNA by a virally encoded reverse transcriptase that is carried as a protein in each retrovirus. The viral DNA is then integrated pseudorandomly into the host cell genome of the infecting cell, forming a "provirus" which is inherited by daughter cells. A number of retroviral systems have been described (U.S. Pat. No. 5,219,740; Miller and Rosman, *BioTechniques* (1989) 7:980–990; Miller, A. D., *Human Gene Therapy* (1990) 1:5–14; Scarpa et al., *Virology* (1991) 180:849–852; Burns et al., *Proc. Natl. Acad. Sci. USA* (1993) 90:8033–8037; and Boris-Lawrie and Temin, *Cur. Opin. Genet. Develop.* (1993) 3:102–109). Retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110–2209), or isolated from known sources using commonly available techniques. Any of the above retroviruses may be readily utilized in order to assemble or construct retroviral gene delivery vehicles given the disclosure provided herein, and standard recombinant techniques (e.g., Sambrook et al, *Molecular Cloning: A Laboratory Manual*, 2d ed., Cold Spring Harbor Laboratory Press, 1989; Kunkle, *PNAS* 82:488, 1985).

Within one aspect of the present invention, retroviral gene delivery vehicles are provided which are constructed to carry or express a selected gene(s) or sequence(s) of interest and in which translation of the gene of interest (transgene) can be regulated by a TOP. In addition, within certain embodiments of the invention, portions of the retroviral gene delivery vehicles may be derived from different retroviruses. For example, within one embodiment of the invention, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus or other like combinations. The constructs may include a 5' LTR, a tRNA binding site, a packaging signal, one or more heterologous sequences, an origin of second strand DNA synthesis and a 3' LTR, wherein the vector construct lacks gag/pol or env coding sequences. As noted above, various promoters, for example tissue-specific, inducible, viral (e.g., CMV or SV40) promoters and/or enhancers can be utilized to drive expression of one or more genes of interest.

Retrovirus vector constructs for use with the subject invention may be generated such that more than one gene of interest is expressed. This may be accomplished through the use of di- or oligo-cistronic cassettes (e.g., where the coding regions are separated by 120 nucleotides or less, see generally Levin et al., *Gene* 108:167–174, 1991), or through the use of Internal Ribosome Entry Sites ("IRES").

Within one aspect of the invention, self-inactivating (SIN) vectors are made by deleting promoter and enhancer elements in the U3 region of the 3' LTR, including the TATA box and binding sites for one or more transcription factors. The deletion is transferred to the 5' LTR after reverse transcription and integration in transduced cells. This results in the transcriptional inactivation of the LTR in the provirus. Possible advantages of SIN vectors include increased safety of the gene delivery system as well as the potential to reduce promoter interference between the LTR and the internal promoter which may result in increased expression of the gene of interest. Furthermore, it is reasonable to expect tighter control of regulatable gene therapy vectors due to the lack of an upstream promoter element in the 5' LTR.

4.D. Adeno-associated Virus Vectors

Adeno-associated virus (AAV) vector systems also find use in the present invention. A variety of AAV vectors have been developed for gene delivery and can be readily constructed using techniques well known in the art in view of the teachings herein. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al., *Molec. Cell. Biol.* (1988) 8:3988–3996; Vincent et al., *Vaccines* 90 (1990) (Cold Spring Harbor Laboratory Press); Carter, B. J. *Current Opinion in Biotechnology* (1992) 3:533–539; Muzyczka, N. *Current Topics in Microbiol. and Immunol.* (1992) 158:97–129; Kotin, R. M. *Human Gene Therapy* (1994) 5:793–801; Shelling and Smith, *Gene Therapy* (1994) 1:165–169; and Zhou et al., *J. Exp. Med.* (1994) 179:1867–1875.

Thus, recombinant AAV vectors which contain a TOP are also included in the scope of the invention. As with other viral vectors, the TOP sequence is typically included in the rAAV vector such that the vector contains the following sequences: an AAV inverted terminal repeat (ITR), a promoter driving mRNA for the transgene, a TOP sequence at the 5' end of the mRNA, a transgene, a polyadenylation signal, and a $2^{nd}$ ITR (FIG. 8). Optionally, an intron is included in the vector and can be inserted anywhere in the transgene mRNA 3' of the TOP sequence. Preferably, there is no untranslated sequence on the 5' side of the TOP and a short untranslated sequence located between the Top and the AUG.

AAV virions can be produced from the TOP-containing vector by providing a suitable packaging cell line, for example, 293, HeLa, CV1 and KB. The TOP-binding ligand (e.g., coat protein) may be produced constitutively or transiently. Constitutive expression of the coat protein may be obtained from the CPP cell line as described above for adenovirus virion construction. Thus, the packaging cell line can constitutively express MS2 coat protein and can be made by standard techniques of transfection followed by selection starting with a rAAV packaging cell line. The rAAV genome is carried on and introduced into the cell line on a plasmid, as a packaged rAAV, or on an adenovirus. In the adenovirus case, rAAV genome would be inserted into the E1 or E3 regions of the virus by standard techniques. Since the transgene carried in the rAAV may have a negative effect on production of such a carrier adenovirus vector, the adenovirus vector could be produce on a coat protein expressing cell line such as CPP. CPP may also be co-transfected with an AAV packaging plasmid containing rep and cap but no ITR's, or with 2 plasmids containing rep on one and cap on the other; plus a rAAV vector with a TOP, and a third plasmid containing the helper functions for AAV growth. Alternatively, the helper functions can be provided by a helper virus such as adenovirus or herpes virus.

Alternatively, coat protein may be supplied using transient transfection techniques, for example, by including an expression plasmid to make coat protein in addition the TOP rAAV vector plasmid, packaging plasmid(s) and helper functions. Thus, transgene expression can be suppressed during production of rAAV virions.

Other viral vector systems which may be used in the present invention include enterically administered recombinant poxvirus vaccines described by Small, Jr., P. A., et al. (U.S. Pat. No. 5,676,950, issued Oct. 14, 1997, herein incorporated by reference); vectors derived from the pox family of viruses, including vaccinia virus and avian poxvirus (See, e.g., WO 91/12882; WO 89/03429; and WO 92/03545) and molecular conjugate vectors, such as the adenovirus chimeric vectors described in Michael et al., *J. Biol. Chem.* (1993) 268:6866–6869 and Wagner et al., *Proc. Natl. Acad. Sci. USA* (1992) 89:6099–6103. Furthermore, as will be apparent to those of skill in the art in view of teachings herein, the products and methods described herein will be applicable to virtually any viral vector.

5. Heterologous Sequences (Transgenes)

As briefly noted above, a wide variety of heterologous sequences may be included within the alphavirus vectors described herein including, for example, sequences which encode palliatives such as lymphokines or cytokines, toxins, and prodrug converting enzymes, sequences which encode antigens that stimulate an immune response, ribozymes or antisense sequences, sequences which encode proteins for therapeutic application such as growth or regulatory factors, and sequences which encode proteins that assist or inhibit an immune response. Preferably, the nucleotide sequences should be of a size sufficient to allow efficient production of viable virions. A wide variety of nucleic acid molecules may be carried and/or expressed by the viral vectors and resulting vector particles. As used herein, "pathogenic agent" refers to a cell that is responsible for a disease state. Representative examples of pathogenic agents include tumor cells, autoreactive immune cells, hormone secreting cells, cells which lack a finction that they would normally have, cells that have an additional inappropriate gene expression which does not normally occur in that cell type, and cells infected with bacteria, viruses, or other intracellular parasites. In addition, as used herein "pathogenic agent" may also refer to a cell that has become tumorigenic due to inappropriate insertion of nucleic acid molecules contained by the viral vector into a host cell's genome.

Examples of nucleic acid molecules which may be carried and/or expressed by viral vectors of the present invention include genes and other nucleic acid molecules which encode a substance lacking in a particular disease state, nucleic acid molecules that encode antigens to provide an immune response, as well as biologically active nucleic acid molecules such as inactivating sequences that incorporate into a specified intracellular nucleic acid molecule and inactivate that molecule. A nucleic acid molecule is considered to be biologically active when the molecule itself provides the desired benefit. For example, the biologically active nucleic acid molecule may be an inactivating sequence that incorporates into a specified intracellular nucleic acid molecule and inactivates that molecule, or the molecule may be a tRNA, rRNA or mRNA that has a configuration that provides a binding capability.

Substances which may be encoded by the nucleic acid molecules described herein include proteins (e.g., antibodies including single chain molecules), immunostimulatory molecules (such as antigens) immunosuppressive molecules, blocking agents, palliatives (such as toxins, antisense ribonucleic acids, ribozymes, enzymes, and other material capable of inhibiting a function of a pathogenic agent) cytokines, various polypeptides or peptide hormones, their agonists or antagonists, where these hormones can be derived from tissues such as the pituitary, hypothalamus, kidney, endothelial cells, liver, pancreas, bone, hemopoetic marrow, and adrenal. Such polypeptides can be used for induction of growth, regression of tissue, suppression of immune responses, apoptosis, gene expression, blocking receptor-ligand interaction, immune responses and can be treatment for certain anemias, diabetes, infections, high blood pressure, abnormal blood chemistry or chemistries (e.g., elevated blood cholesterol, deficiency of blood clotting factors, elevated LDL with lowered HDL), levels of Alzheimer associated amyloid protein, bone erosion/calcium deposition, and controlling levels of various metabolites such as steroid hormones, purines, and pyrimidines.

For palliatives, when "capable of inhibiting a function" is utilized within the context of the present invention, it should be understood that the palliative either directly inhibits the function or indirectly does so, for example, by converting an agent present in the cells from one which would not normally inhibit a function of the pathogenic agent to one which does. Examples of such functions for viral diseases include adsorption, replication, gene expression, assembly, and exit of the virus from infected cells. Examples of such functions for cancerous diseases include cell replication, susceptibility to external signals (e.g., contact inhibition), and lack of production of anti-oncogene proteins. Examples of such functions for cardiovascular disease include inappropriate growth or accumulation of material in blood vessels, high blood pressure, undesirable blood levels of factors such as cholesterol or low density lipoprotein that predispose to disease, localized hypoxia, and inappropriately high and tissue-damaging levels of free radicals. Examples of such functions for neurological conditions include pain, lack of dopamine production, inability to replace damaged cells, deficiencies in motor control of physical activity, inappropriately low levels of various peptide hormones derived from neurological tissue such as the pituitary or hypothalamus, accumulation of Alzheimer's Disease associated amyloid plaque protein, and inability to regenerate damaged nerve junctions. Examples of such functions for autoimmune or inflammatory disease include inappropriate production of cytokines and lymphokines, inappropriate production and existence of autoimmune antibodies and cellular immune responses, inappropriate disruption of tissues by proteases and collagenases, lack of production of factors normally supplied by destroyed cells, and excessive or aberrant regrowth of tissues under autoimmune attack.

Representative examples of palliatives that act directly to inhibit the growth of cells include toxins such as ricin (Lamb et al., *Eur. J. Biochem.* 148:265–270, 1985), abrin (Wood et al., *Eur. J. Biochem.* 198:723–732, 1991; Evensen et al., *J. of Biol. Chem.* 266:6848–6852, 1991; Collins et al., *J. of Biol. Chem.* 265:8665–8669, 1990; Chen et al., *Fed. of Eur. Biochem Soc.* 309:115–118, 1992), diphtheria toxin (Tweten et al., *J. Biol. Chem.* 260:10392–10394, 1985), cholera toxin (Mekalanos et al., *Nature* 306:551–557, 1983; Sanchez & Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), antiviral protein (Barbieri et al., *Biochem. J.* 203:55–59, 1982; Irvin et al., *Arch. Biochem. & Biophys.* 200:418–425, 1980; Irvin, *Arch. Biochem. & Biophys.* 169:522–528, 1975), tritin, Shigella toxin (Calderwood et al., *PNAS* 84:4364–4368, 1987; Jackson et al., Microb. Path. 2:147–153, 1987), and Pseudomonas exotoxin A (Carroll and Collier, *J. Biol. Chem.* 262:8707–8711, 1987). A detailed description of recombinant retroviruses which express Russel's Viper Venom is provided in U.S. Ser. No. 08/368,574, filed Dec. 30, 1994.

Within other aspects of the invention, the viral vector carries a gene specifying a product which is not in itself toxic, but when processed or modified by a protein, such as a protease specific to a viral or other pathogen, is converted into a toxic form. For example, recombinant retrovirus could carry a gene encoding a proprotein chain, which becomes toxic upon processing by the retroviral protease. More specifically, a synthetic inactive proprotein form of the toxic ricin or diphtheria A chains could be cleaved to the active form by arranging for the virally encoded protease to recognize and cleave off an appropriate "pro" element.

Within a related aspect of the present invention, viral vectors are provided which direct the expression of a gene product(s) that activates a compound with little or no cytotoxicity into a toxic product. Briefly, a wide variety of gene products which either directly or indirectly activate a compound with little or no cytotoxicity into a toxic product may be utilized within the context of the present invention. Representative examples of such gene products include HSVTK and VZVTK which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAC, DHPG) to HSVTK, phosphorylates the drug into its corresponding active nucleotide triphosphate form.

In a manner similar to the preceding embodiment, viral vectors may be generated which carry a gene for phosphorylation, phosphoribosylation, ribosylation, or other metabolism of a purine- or pyrimidine-based drug. Such genes may have no equivalent in mammalian cells, and might come from organisms such as a virus, bacterium, fungus, or protozoan. Representative examples include: *E. coli* guanine phosphoribosyl transferase ("gpt") gene product, which converts thioxanthine into thioxanthine monophosphate (see Besnard et al., *Mol. Cell. Biol.* 7:4139–4141, 1987); alkaline phosphatase, which will convert inactive phosphorylated compounds such as mitomycin phosphate and doxorubicin-phosphate to toxic dephosphorylated compounds; fungal (e.g., *Fusarium oxysporum*) or bacterial cytosine deaminase which will convert 5-fluorocytosine to the toxic compound 5-fluorouracil (Mullen, *PNAS* 89:33, 1992); carboxypeptidase G2 which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds.

Conditionally lethal gene products of this type have application to many presently known purine- or pyrimidine-based anticancer drugs, which often require intracellular ribosylation or phosphorylation in order to become effective cytotoxic agents. The conditionally lethal gene product could also metabolize a nontoxic drug, which is not a purine or pyrimidine analogue, to a cytotoxic form (see Searle et al., *Brit. J. Cancer* 53:377–384, 1986).

Additionally, in the instance where the target pathogen is a mammalian virus, vectors may be constructed to take advantage of the fact that mammalian viruses in general tend to have "immediate early" genes, which are necessary for subsequent transcriptional activation of other viral promoter elements. Gene products of this nature are excellent candidates for intracellular signals (or "identifying agents") of viral infection. Thus, conditionally lethal genes transcribed from transcriptional promoter elements that are responsive to such viral "immediate early" gene products could specifically kill cells infected with any particular virus. Additionally, since the human and interferon promoter elements are transcriptionally activated in response to infection by a wide variety of nonrelated viruses, the introduction of vectors expressing a conditionally lethal gene product like HSVTK, for example, from these viral-responsive elements (VREs) could result in the destruction of cells infected with a variety of different viruses.

In another embodiment of the invention, viral vectors are provided that produce substances such as inhibitor palliatives, that inhibit viral assembly. In this context, the recombinant retrovirus codes for defective gag, pol, env or other viral particle proteins or peptides which inhibit in a dominant fashion the assembly of viral particles. Such inhibition occurs because the interaction of normal subunits of the viral particle is disturbed by interaction with the defective subunits.

One way of increasing the effectiveness of inhibitory palliatives is to express inhibitory genes, such as viral inhibitory genes, in conjunction with the expression of genes which increase the probability of infection of the resistant cell by the virus in question. The result is a nonproductive "dead-end" event which would compete for productive infection events.

In another embodiment of the invention, viral vectors are provided for the expression substances such as inhibiting peptides or proteins specific for viral protease. Viral protease cleaves the viral gag and gag/pol proteins into a number of smaller peptides. Failure of this cleavage in all cases leads to complete inhibition of production of infectious retroviral particles. The HIV protease is known to be an aspartyl protease, and these are known to be inhibited by peptides made from amino acids from protein or analogues. Viral vectors that inhibit HIV will express one or multiple fused copies of such peptide inhibitors.

In yet another aspect, viral vectors are provided which have a therapeutic effect by encoding one or more ribozymes (RNA enzymes) (Haseloff and Gerlach, Nature 334:585, 1989) which will cleave, and hence inactivate, RNA molecules corresponding to a pathogenic function. Since ribozymes function by recognizing a specific sequence in the target RNA and this sequence is normally 12 to 17 bp, this allows specific recognition of a particular RNA sequence corresponding to a pathogenic state, such as HIV tat, and toxicity is specific to such pathogenic state. Representative examples of suitable ribozymes include hammerhead ribozymes (see Rossi et al., Pharmac. Ther 50:245–254, 1991) and hairpin ribozymes (Hampel et al., Nucl. Acids Res. 18:299–304, 1990; U.S. Pat. No. 5,254,678) and Tetrahymena based ribozymes (U.S. Pat. No. 4,987,071). Additional specificity may be achieved in some cases by making this a conditional toxic palliative, as discussed above.

In still another aspect, viral vectors are provided comprising a biologically active nucleic acid molecule that is an antisense sequence (an antisense sequence may also be encoded by a nucleic acid sequence and then produced within a host cell via transcription). Briefly, antisense sequences are designed to bind to RNA transcripts, and thereby prevent cellular synthesis of a particular protein, or prevent use of that RNA sequence by the cell.

Representative examples of such sequences include antisense thymidine kinase, antisense dihydrofolate reductase (Maher and Dolnick, Arch. Biochem. & Biophys. 253:214–220, 1987; Bzik et al., PNAS 84:8360–8364, 1987), antisense HER2 (Coussens et al., Science 230:1132–1139, 1985), antisense ABL (Fainstein et al., Oncogene 4:1477–1481, 1989), antisense Myc (Stanton et al., Nature 310:423–425, 1984) and antisense ras, as well as antisense sequences which block any of the enzymes in the nucleotide biosynthetic pathway. In other embodiments, the antisense sequence is selected from the group consisting of sequences which encode influenza virus, HIV, HSV, HPV, CMV, and HBV. The antisense sequence may also be an antisense RNA complementary to RNA sequences necessary for pathogenicity. Alternatively, the biologically active nucleic acid molecule may be a sense RNA (or DNA) complementary to RNA sequences necessary for pathogenicity.

Within a further embodiment of the invention antisense RNA may be utilized as an anti-tumor agent in order to induce a potent Class I restricted response. Briefly, in addition to binding RNA and thereby preventing translation of a specific mRNA, high levels of specific antisense sequences are believed to induce the increased expression of interferons (including gamma-interferon), due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

In another embodiment, viral vectors of the invention express a surface protein that is itself therapeutically beneficial. For example, in the particular case of HIV, expression of the human CD4 protein specifically in HIV-infected cells may be beneficial in two ways:

1. Binding of CD4 to HIV env intracellularly could inhibit the formation of viable viral particles much as soluble CD4 has been shown to do for free virus, but without the problem of systematic clearance and possible immunogenicity, since the protein will remain membrane bound and is structurally identical to endogenous CD4 (to which the patient should be immunologically tolerant).

2. Since the CD4/HIV env complex has been implicated as a cause of cell death, additional expression of CD4 (in the presence of excess HIV-env present in HIV-infected cells) leads to more rapid cell death and thus inhibits viral dissemination. This may be particularly applicable to monocytes and macrophages, which act as a reservoir for virus production as a result of their relative refractility to HIV-induced cytotoxicity (which, in turn, is apparently due to the relative lack of CD4 on their cell surfaces).

Still farther aspects of the present invention relate to viral vectors capable of immunostimulation. Briefly, the ability to recognize and defend against foreign pathogens is essential to the function of the immune system. In particular, the immune system must be capable of distinguishing "self" from "nonself" (i.e., foreign), so that the defensive mechanisms of the host are directed toward invading entities instead of against host tissues. Cytolytic T lymphocytes (CTLs) are typically induced, or stimulated, by the display of a cell surface recognition structure, such as a processed, pathogen-specific peptide, in conjunction with a MHC class I or class II cell surface protein.

Diseases suitable to treatment include viral infections such as influenza virus, malaria, respiratory syncytial virus, HPV, HBV, HCV, EBV, HIV, HSV, FeLV, FIV, Hantavirus, HTLV I, HTLV II and CMV, cancers such as melanomas, renal carcinoma, breast cancer, ovarian cancer and other cancers, and heart disease.

In one embodiment, the invention provides methods for stimulating a specific immune response and/or inhibiting viral spread by using viral vectors that direct the expression of an antigen or modified form thereof in susceptible target cells, wherein the antigen is capable of either (1) initiating an immune response to the viral antigen or (2) preventing the viral spread by occupying cellular receptors required for viral interactions. Expression of the protein may be transient or stable with time. Where an immune response is to be stimulated to a pathogenic antigen, the viral vector is preferably designed to express a modified form of the antigen which will stimulate an immune response and which has reduced pathogenicity relative to the native antigen. This immune response is achieved when cells present antigens in the correct manner, i.e., in the context of the MHC class I and/or II molecules along with accessory molecules such as CD3, ICAM-1, ICAM-2, LFA-1, or analogs thereof (e.g., Altmann et al., Nature 338:512, 1989).

An immune response can also be achieved by transferring to an appropriate immune cell (such as a T lymphocyte) (a) the gene for the specific T-cell receptor that recognizes the antigen of interest (in the context of an appropriate MHC molecule if necessary), (b) the gene for an immunoglobulin which recognizes the antigen of interest, or (c) the gene for a hybrid of the two which provides a CTL response in the absence of the MHC context. Thus, recombinant virions may also be used as an immunostimulant, immunomodulator, or vaccine, etc.

In the particular case of disease caused by HIV infection, where immunostimulation is desired, the antigen generated from a recombinant virions may be in a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but haplotype-specific epitopes or to present several haplotype-specific epitopes, and allow a response capable of eliminating cells infected with most or all strains of HIV. The haplotype-specific epitopes can be further selected to promote the stimulation of an immune response within an animal which is cross-reactive against other strains of HIV. Antigens from other HIV genes or combinations of genes, such as gag, pol, rev, vif, nef, prot, gag/pol, gag prot, etc., may also provide protection in particular cases.

HIV is only one example. This approach may be utilized for many virally linked diseases or cancers where a characteristic antigen (which does not need to be a membrane protein) is expressed. Representative examples of such "disease-associated" antigens all or portions of various eukaryotic (including for example, parasites), prokaryotic (e.g., bacterial) or viral pathogens. Representative examples of viral pathogens include the Hepatitis B Virus ("HBV"; see, e.g., Valenenzuela et al. (1980) *"The Nucleotide Sequence of the Hepatitis B Viral Genome and the Identification of the Major Viral Genes"* in *Animal Virus Genetics* pp. 57–70; Valenenzuela et al. (1979) *Nature* 280:815–819) and Hepatitis C Virus ("HCV"; see, e.g., Chien et al., International Publication No. WO 93/00365; Chien, D. Y., International Publication No. WO 94/01778), Human Papilloma Virus ("HPV"; see WO 92/05248; WO 90/10459; EPO 133,123), Epstein-Barr Virus ("EBV"; see EPO 173, 254; JP 1,128,788; and U.S. Pat. Nos. 4,939,088 and 5,173, 414), Feline Leukemia Virus ("FeLV"; see EPO 377,842; WO 90/08832; WO 93/09238), Feline Immunodeficiency Virus ("FIV"; U.S. Pat. No. 5,037,753; WO 92/15684; WO 90/13573; and JP 4,126,085), HTLV I and II, and Human Immunodeficiency Virus ("HIV"; see U.S. Ser. No. 07/965, 084, now abandoned).

In accordance with the immunostimulation aspects of the invention, substances which are carried and/or expressed by the viral vectors of the present invention may also include "immunomodulatory factors," many of which are set forth above. Immunomodulatory factors refer to factors that, when manufactured by one or more of the cells involved in an immune response, or, which when added exogenously to the cells, causes the immune response to be different in quality or potency from that which would have occurred in the absence of the factor. The factor may also be expressed from a non-recombinant viral derived gene, but the expression is driven or controlled by the recombinant virus. The quality or potency of a response may be measured by a variety of assays known to one of skill in the art including, for example, in vitro assays which measure cellular proliferation (e.g., $^3$H thymidine uptake), and in vitro cytotoxic assays (e.g., which measure $^{51}$Cr release) (see, Warner et al., *AIDS Res. and Human Retroviruses* 7:645–655, 1991). Immunomodulatory factors may be active both in vivo and ex vivo.

Representative examples of such factors include cytokines, such as IL-1, IL-2 (Karupiah et al., *J. Immunology* 144:290–298, 1990; Weber et al., *J. Exp. Med.* 166:1716–1733, 1987; Gansbacher et al., *J. Exp. Med.* 172:1217–1224, 1990; U.S. Pat. No. 4,738,927), IL-3, IL-4 (Tepper et al., *Cell* 57:503–512, 1989; Golumbek et al., *Science* 254:713–716, 1991; U.S. Pat. No. 5,017,691), IL-5, IL-6 (Brakenhof et al., *J. Immunol.* 139:4116–4121, 1987; WO 90/06370), IL-7 (U.S. Pat. No. 4,965,195), IL-8, IL-9, IL-10, IL- 11, IL-12, IL-13 (*Cytokine Bulletin*, Summer 1994), IL-14 and IL-15, particularly IL-2, IL-4, IL-6, IL-12, and IL-13, alpha interferon (Finter et al., *Drugs* 42(5): 749–765, 1991; U.S. Pat. No. 4,892,743; U.S. Pat. No. 4,966,843; WO 85/02862; Nagata et al., *Nature* 284:316–320, 1980; Familletti et al., *Methods in Enz.* 78:387–394,1981; Twu et al., *Proc. Natl. Acad. Sci. USA* 86:2046–2050,1989; Faktor et al., *Oncogene* 5:867–872, 1990), beta interferon (Seif et al., *J. Virol.* 65:664–671, 1991), gamma interferons (Radford et al., *The American Society of Hepatology* 2008–2015, 1991; Watanabe et al., *PNAS* 86:9456–9460, 1989; Gansbacher et al., *Cancer Research* 50:7820–7825, 1990; Maio et al., *Can. Immunol. Immunother*. 30:34–42, 1989; U.S. Pat. No. 4,762,791; U.S. Pat. No. 4,727,138), G-CSF (U.S. Pat. Nos. 4,999,291 and 4,810,643), GM-CSF (WO 85/04188), tumor necrosis factors (TNFs) (Jayaraman et al., *J. Immunology* 144:942–951, 1990), CD3 (Krissanen et al.,*Immunogenetics* 26:258–266, 1987), ICAM-1 (Altman et al., *Nature* 338:512–514, 1989; Simmons et al., *Nature* 331:624–627, 1988), ICAM-2, LFA-1, LFA-3 (Wallner et al., *J. Exp. Med.* 166(4):923–932, 1987), MHC class I molecules, MHC class II molecules, B7.1–.3, $b_2$-microglobulin (Parnes et al., *PNAS* 78:2253–2257, 1981), chaperones such as calnexin, MHC linked transporter proteins or analogs thereof (Powis et al., *Nature* 354:528–531, 1991). Immunomodulatory factors may also be agonists, antagonists, or ligands for these molecules. For example soluble forms of receptors can often behave as antagonists for these types of factors, as can mutated forms of the factors themselves.

The choice of which immunomodulatory factor to include within a viral vector may be based upon known therapeutic effects of the factor, or, experimentally determined. For example, a known therapeutic effector in chronic hepatitis B infections is alpha interferon. This has been found to be efficacious in compensating a patient's immunological deficit, and thereby assisting recovery from the disease. Alternatively, a suitable immunomodulatory factor may be experimentally determined. Briefly, blood samples are first taken from patients with a hepatic disease. Peripheral blood lymphocytes (PBLs) are restimulated in vitro with autologous or HLA matched cells (e.g., EBV transformed cells) that have been transduced with a recombinant virus which directs the expression of an immunogenic portion of a hepatitis antigen and the immunomodulatory factor. These stimulated PBLs are then used as effectors in a CTL assay with the HLA matched transduced cells as targets. An increase in CTL response over that seen in the same assay performed using HLA matched stimulator and target cells transduced with a vector encoding the antigen alone, indicates a useful immunomodulatory factor. Within one embodiment of the invention, the immunomodulatory factor gamma interferon is particularly preferred.

The present invention also includes vectors which encode immunogenic portions of desired antigens including, for example, viral, bacterial or parasite antigens. For example, at least one immunogenic portion of a hepatitis B antigen can be incorporated into an vector. The immunogenic portion(s) which are incorporated into the vector may be of varying length, although it is generally preferred that the portions be at least 9 amino acids long, and may include the entire antigen. Immunogenicity of a particular sequence is often difficult to predict, although T cell epitopes may be predicted utilizing the HLA A2.1 motif described by Falk et al. (*Nature* 351:290, 1991). From this analysis, peptides may be synthesized and used as targets in an in vitro cytotoxic assay. Other assays, however, may also be utilized, including, for example, ELISA which detects the presence of antibodies against the newly introduced vector, as well as assays which test for T helper cells, such as gamma-interferon assays, IL-2 production assays, and proliferation assays.

Within one embodiment of the present invention, at least one immunogenic portion of a hepatitis C antigen can be incorporated into a viral vector. Preferred immunogenic portion(s) of hepatitis C may be found in the C and NS3–NS4 regions since these regions are the most conserved among various types of hepatitis C virus (loughton et al., *Hepatology* 14:381–388, 1991). Particularly preferred immunogenic portions may be determined by a variety of methods. For example, as noted above for the hepatitis B virus, identification of immunogenic portions of the polypeptide may be predicted based upon amino acid sequence. Briefly, various computer programs which are known to those of ordinary skill in the art may be utilized to predict CTL epitopes. For example, CTL epitopes for the HLA A2.1 haplotype may be predicted utilizing the HLA A2.1 motif described by Falk et al. (*Nature* 351:290, 1991). From this analysis, peptides are synthesized and used as targets in an in vitro cytotoxic assay.

Other disease-associated antigens which may be carried by the gene delivery constructs of the present invention include, for example immunogenic, non-tumorigenic forms of altered cellular components which are normally associated with tumor cells (see U.S. Ser. No. 08/104,424, now abandoned). Representative examples of altered cellular components which are normally associated with tumor cells include ras* (wherein "*" is understood to refer to antigens which have been altered to be non-tumorigenic), p53*, Rb*, altered protein encoded by Wilms' tumor gene, ubiquitin*, mucin, protein encoded by the DCC. APC, and MCC genes, as well as receptors or receptor-like structures such as neu, thyroid hormone receptor, Platelet Derived Growth Factor ("PDGF") receptor, insulin receptor, Epidermal Growth Factor ("EGF") receptor, and the Colony Stimulating Factor ("CSF") receptor.

Immunogenic portions of the disease-associated antigens described herein may be selected by a variety of methods. For example, the HLA A2.1/$K^b$ transgenic mouse has been shown to be useful as a model for human T-cell recognition of viral antigens. Briefly, in the influenza and hepatitis B viral systems, the murine T-cell receptor repertoire recognizes the same antigenic determinants recognized by human T-cells. In both systems, the CTL response generated in the HLA A2.1/$K^b$ transgenic mouse is directed toward virtually the same epitope as those recognized by human CTLs of the HLA A2.1 haplotype (Vitiello et al., *J. Exp. Med.* 173:1007–1015, 1991; Vitiello et al., *Abstract of Molecular Biology of Hepatitis B Virus Symposia*, 1992).

Immunogenic proteins of the present invention may also be manipulated by a variety of methods known in the art, in order to render them more immunogenic. Representative examples of such methods include: adding amino acid sequences that correspond to T helper epitopes; promoting cellular uptake by adding hydrophobic residues; by forming particulate structures; or any combination of these (see generally, Hart, op. cit., Milich et al., *Proc. Natl. Acad. Sci. USA* 85:1610–1614, 1988; Willis, *Nature* 340:323–324, 1989; Griffiths et al., *J. Virol.* 65:450–456, 1991).

Sequences which encode the above-described nucleic acid molecules may be obtained from a variety of sources. For example, plasmids which contain sequences that encode altered cellular products may be obtained from a depository such as the American Type Culture Collection (ATCC, Manassas, Va.), or from commercial sources such as Advanced Biotechnologies (Columbia, Md.). Representative examples of plasmids containing some of the above-described sequences include ATCC No. 41000 (containing a G to T mutation in the 12th codon of ras), and ATCC No. 41049 (containing a G to A mutation in the 12th codon).

Other nucleic acid molecules that encode the above-described substances, as well as other nucleic acid molecules that are advantageous for use within the present invention, may be readily obtained from a variety of sources, including for example depositories such as the American Type Culture Collection (ATCC, Manassas, Va.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Molecularly cloned genomes which encode the hepatitis B virus may be obtained from a variety of sources including, for example, the American Type Culture Collection (ATCC, Manassas, Va.). For example, ATCC No. 45020 contains the total genomic DNA of hepatitis B (extracted from purified Dane particles) (see FIG. 3 of Blum et al., TIG 5(5): 154–158, 1989) in the BamH I site of pBR322 (Moriarty et al., *Proc. Natl. Acad. Sci. USA* 78:2606–2610, 1981). (Note that correctable errors occur in the sequence of ATCC No. 45020.)

Alternatively, cDNA sequences for use with the present invention may be obtained from cells which express or contain the sequences. Briefly, within one embodiment mRNA obtained from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159). See also *PCR Technology: Principles and Applications for DNA Amplification*, Erlich (ed.), Stockton Press, 1989) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Nucleic acid molecules which are carried and/or expressed by the viral vectors described herein may also be synthesized, for example, on an Applied Biosystems Inc. DNA synthesizer (e.g., APB DNA synthesizer model 392 (Foster City, Calif.).

EXAMPLES

Example 1

Adenovirus Virion Production

A. Translation Operator Plasmids

A destabilized GFP gene from p EGFP-N I was used as the reporter for this study (Clonetech, Inc). To make the MS2GFP gene the 5' end of GFP was modified by PCR with these primers:

CTGGTTTAGGGATCCGACCATCACCAT-CAGGGATGGTGAGCAAGGGCGAGGA GCTCT-TCACCCGGGTGGTGCCCATC (GFPF, SEQ ID NO:11), and GGGGAATTCTTACTACACATTGATC-CTAGCAG (GFPR, SEQ ID NO:12), digested the DNA with EcoR1, and inserted the product into EcoICRI (Promega, Madison, Wis.) and EcoR1 digested padlox (Hardy et al.). This removed the SacI site from the CMV promoter, inserted a BamH1 site at −23 and a TOP at −16 relative to the GFP ATG, and introduced a silent change in GFP codon 8 inserting a SacI site. The +4 MS2GFP construct was made by treating BamH1 digested pMS2GFP with Klenow DNA polymerase and relegating the plasmid. TOPGFP was made by digesting pMS2GFP with BamH1 and SacI and inserting GATCCGACCAGCACCATCAGGGCTGG-GATATCACCATGGTGAGCAAGGGCGA GGAGCT (topa, SEQ ID NO:13). βutrTOP was made by digesting pTOPGFP with BamH1 plus EcoRV and inserting:

GATCCGACATTTGCTTCTAGACACAACT-GTGTTCACTACCAGCACCATCAGGG CTGGGAT (topb, SEQ ID NO: 14). TOPβutr was made by digesting pTOPGFP with EcoRV plus Sac1 and inserting:

ACATTTGCTTCTGACACAACTGTGT-TCACTAGCAACCTCAAGTATACCATGGT GAG-CAAGGGCGAGGAGCT (topβa, SEQ ID NO:15) TOP2 was made by digesting pTOPGFP with EcoRV and inserting:

AAATAAATAATAGCTGGAGGATCAC-CCCAGTACTGTGAACGAT (topβb, SEQ ID NO:16) in the correct orientation.

Figure 4:
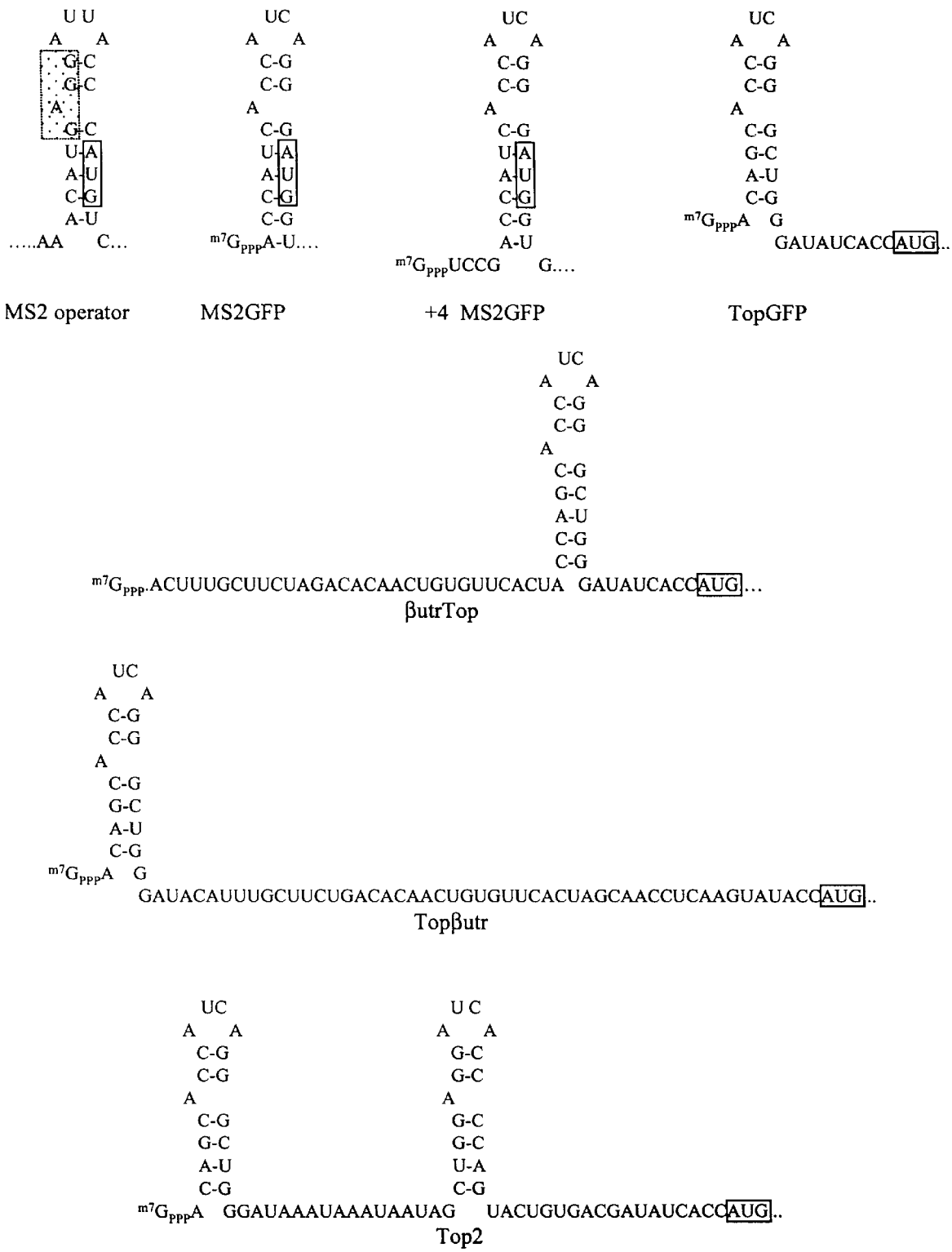
FIG. 4 shows the folded structure of various translational operator sequences (TOP) described in the Examples (SEQ ID NOs:4–10). For the wild type sequence of the MS2 operator, the Shine-Dalgarno sequence is in a stippled box, the starting AUG codons for all TOP's are in a solid boxes and the position of the 5',5',7-methyl guanosine triphosphate cap sequence ($^{m7}$G-cap) is designated. All of the TOP's contain changes relative to the wild type sequence, but the structure that binds to MS2 coat protein is maintained. MS2GFP and +4 MS2GFP have the AUG's in the TOP structure all others have the AUG in a Kozak sequence located downstream of the TOP. The +4 MS2GFP has four bases inserted between the $^{m7}$G cap and the TOP compared to MS2GFP. The βutrTOP and TOPβutr versions have human β-globin 5' UTR included in the positions shown. TOP2 has two TOP's spaced such that cooperative binding of coat protein could occur.
Figure 5A:
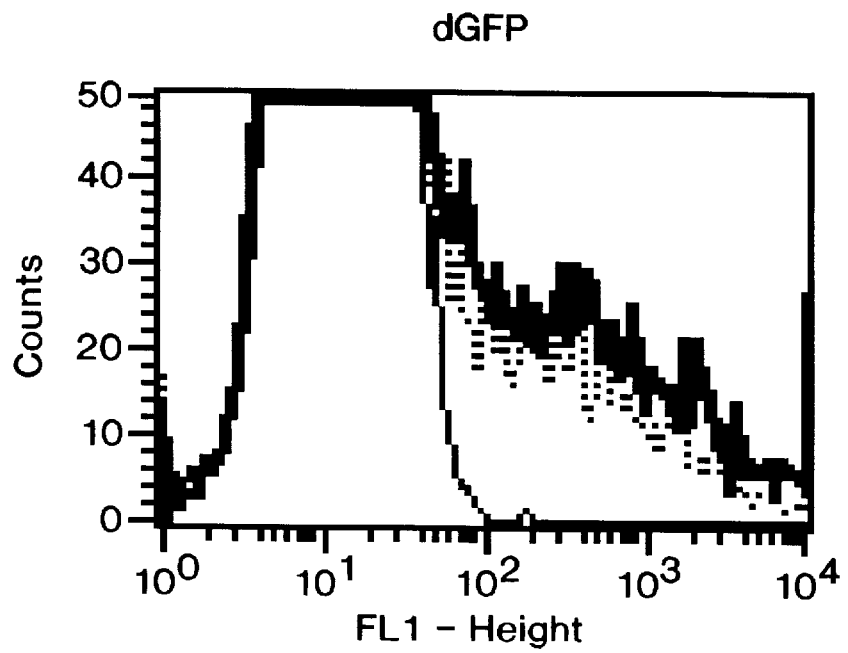
FIGS. 5A through 5G depict FACscan analysis of 293 cells transiently co-transfected with GFP plasmids linked to TOP sequences plus expression plasmids making MS2 coat protein or an irrelevant gene. The position of untransfected cells is shown in each panel (thin, solid line) with the comparison of unsuppressed (thick, solid line) and suppressed (dotted line). Panel A depicts no TOP attached to GFP gene; Panel B depicts MS2GFP, AUG included in TOP sequence; Panel C depicts TOPGFP with a 24 base 5' UTR; Panel D depicts TOPβUTR, 70 base 5' UTR; Panel E depicts +4 MS2GFP, equivalent to MS2GFP with 4 bases inserted between the cap and TOP; Panel F depicts βutrTOP, equivalent to TOPβutr but with the UTR inserted between the cap and the TOP; and Panel G depicts Top2, 2 TOP sequences spaced to allow cooperative binding of coat protein.
Figure 5B:
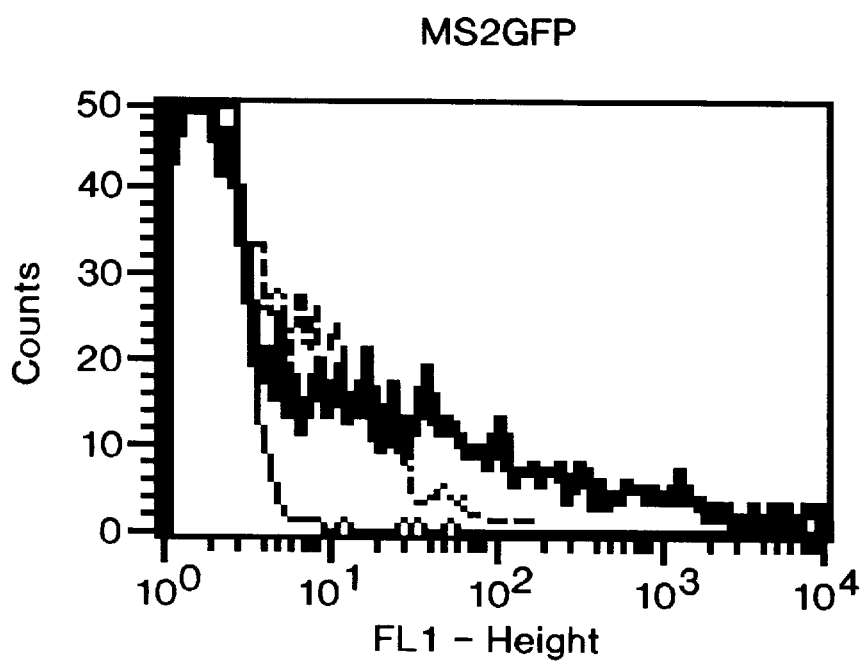
Figure 5C:
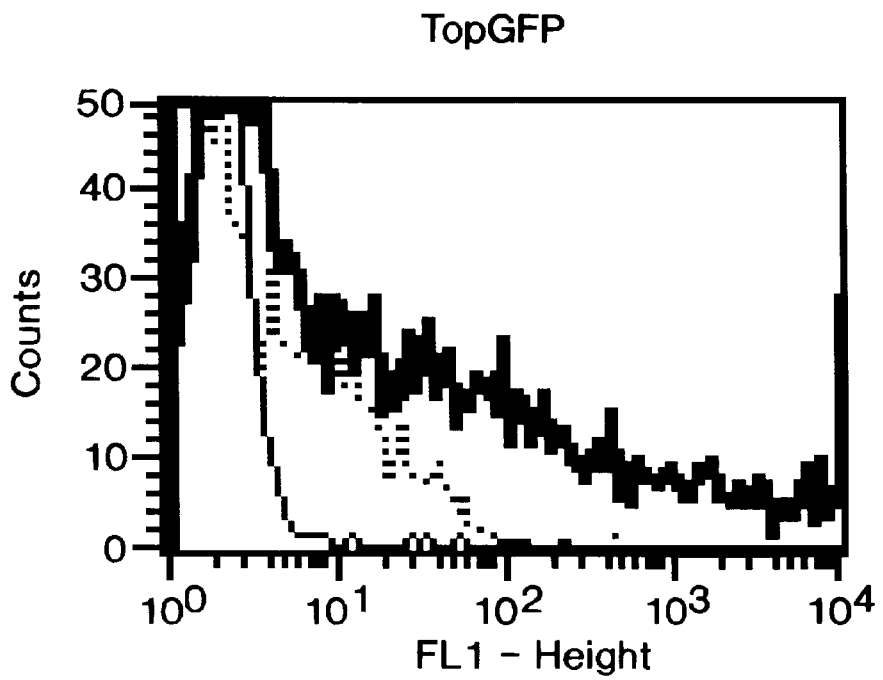
Figure 5D:
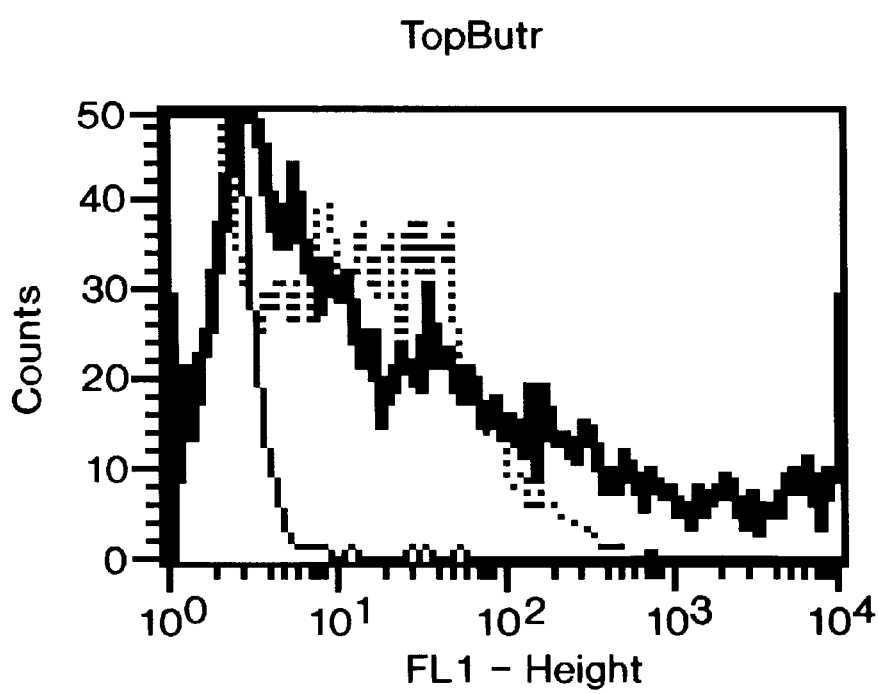
Figure 5E:
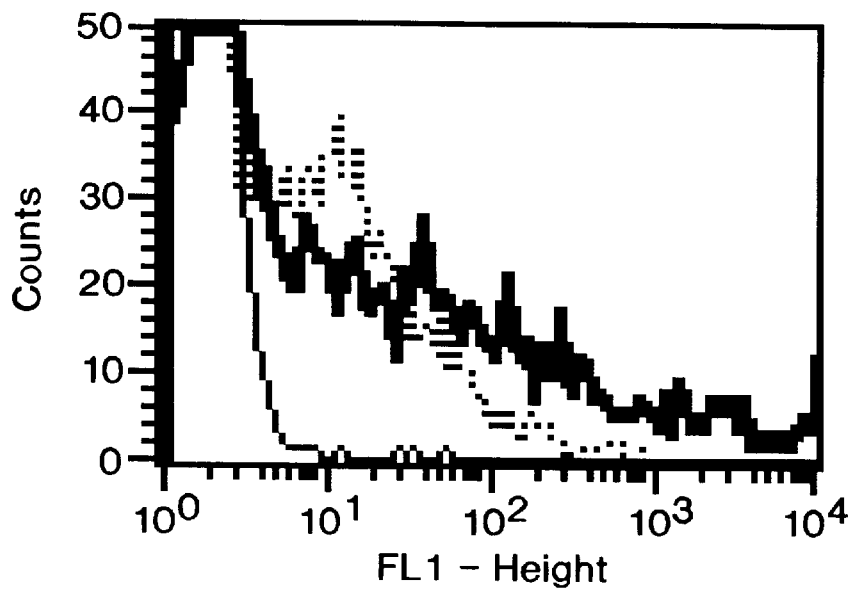
Figure 5F:
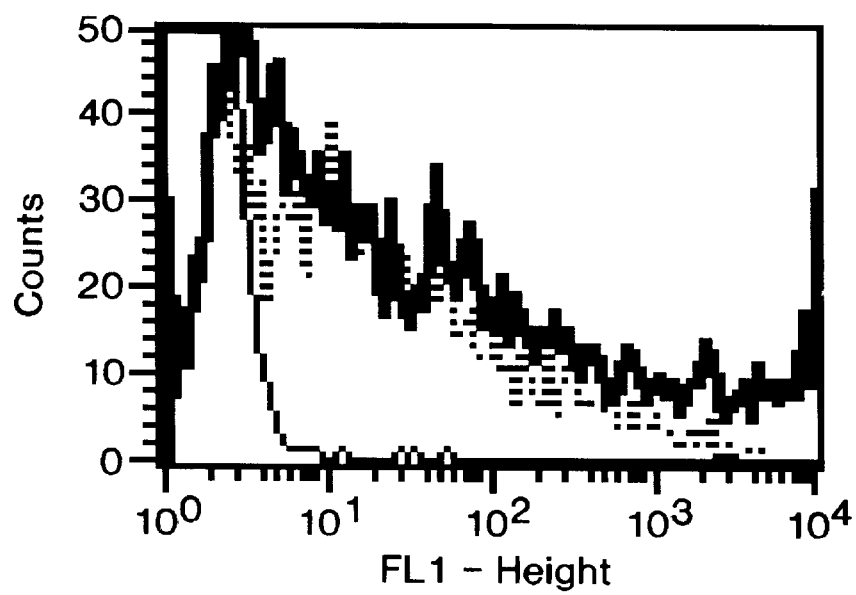
Figure 5G:
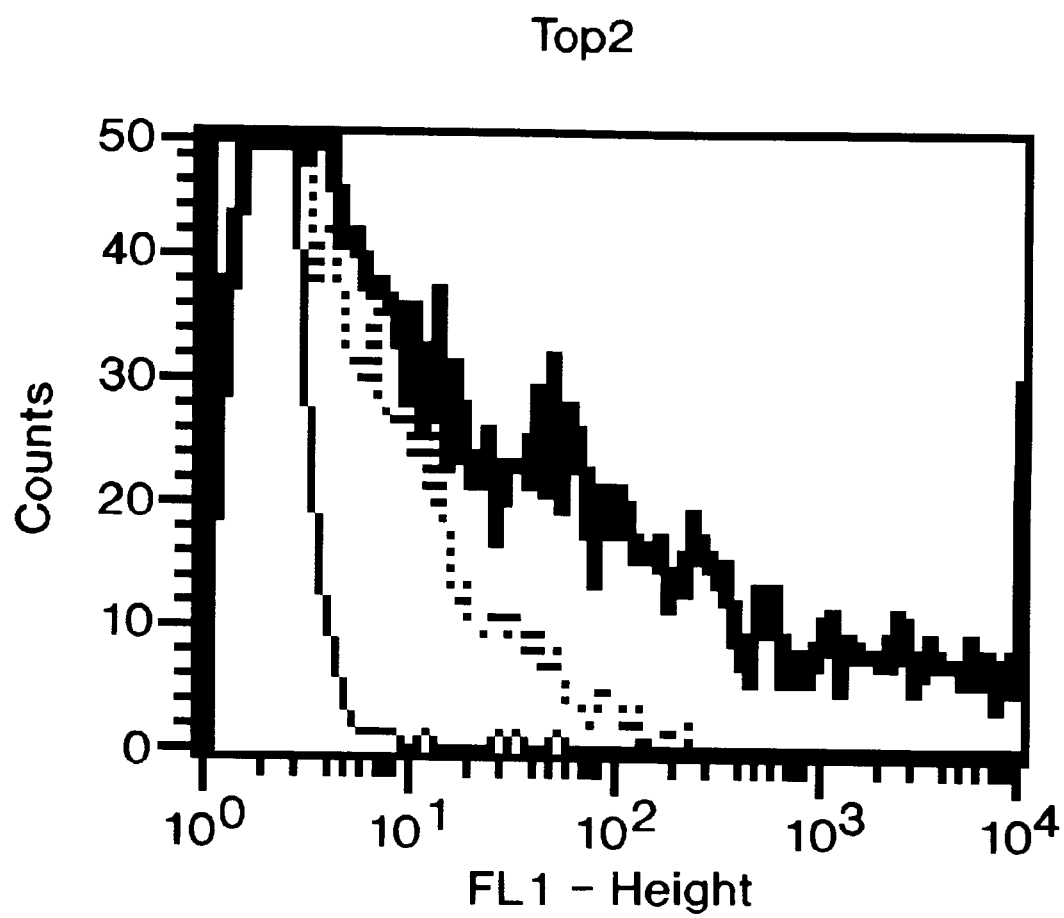
Figure 6A:
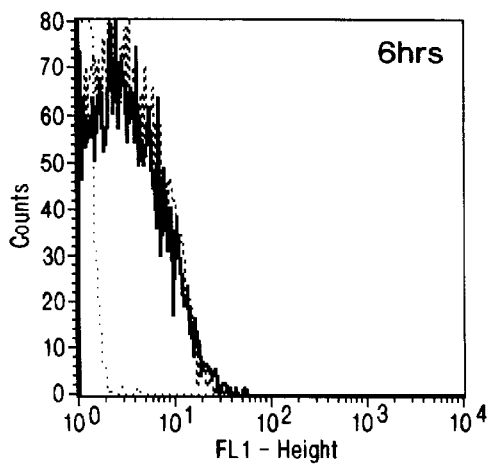
FIGS. 6A through 6E depicts FACscan analysis of cre8 and CPP cells infected with a TOPGFP adenovirus vector. Each cell type was infected with the 200 particles per cell of virus and the cells were removed from the dish and analyzed at the times shown (Panel A at 6 hours; Panel B at 18 hours; Panel C at 24 hours; Panel D at 30 hours; and Panel E at 48 hours). The data has been gated for single live cells.
Figure 6B:
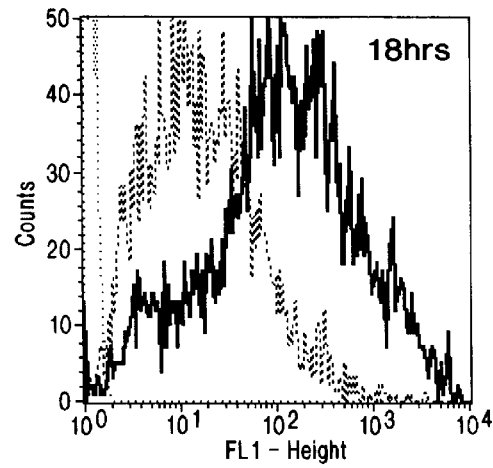
Figure 6C:
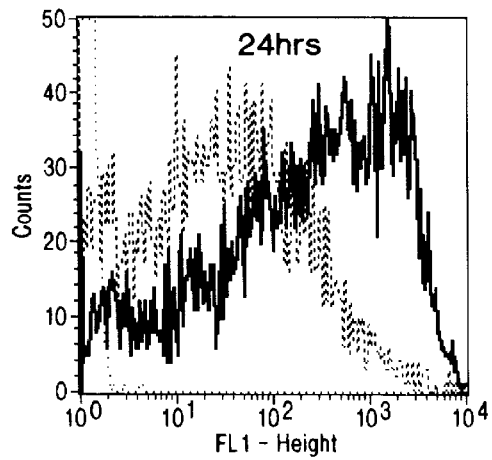
Figure 6D:
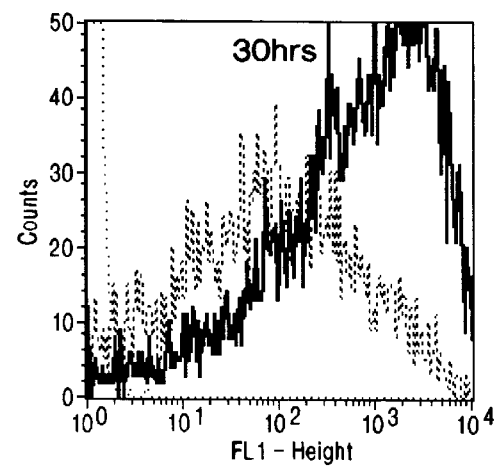
Figure 6E:
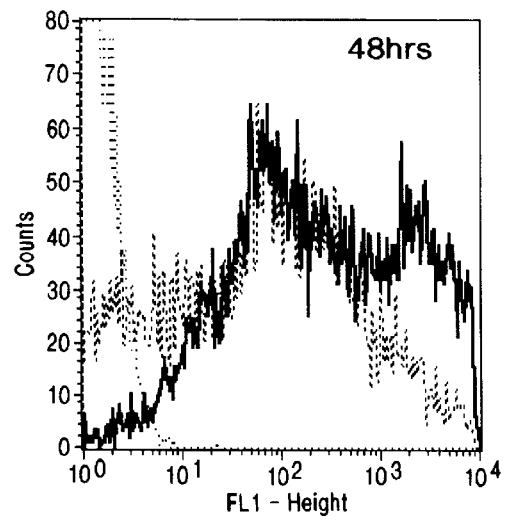
Figure 7A:
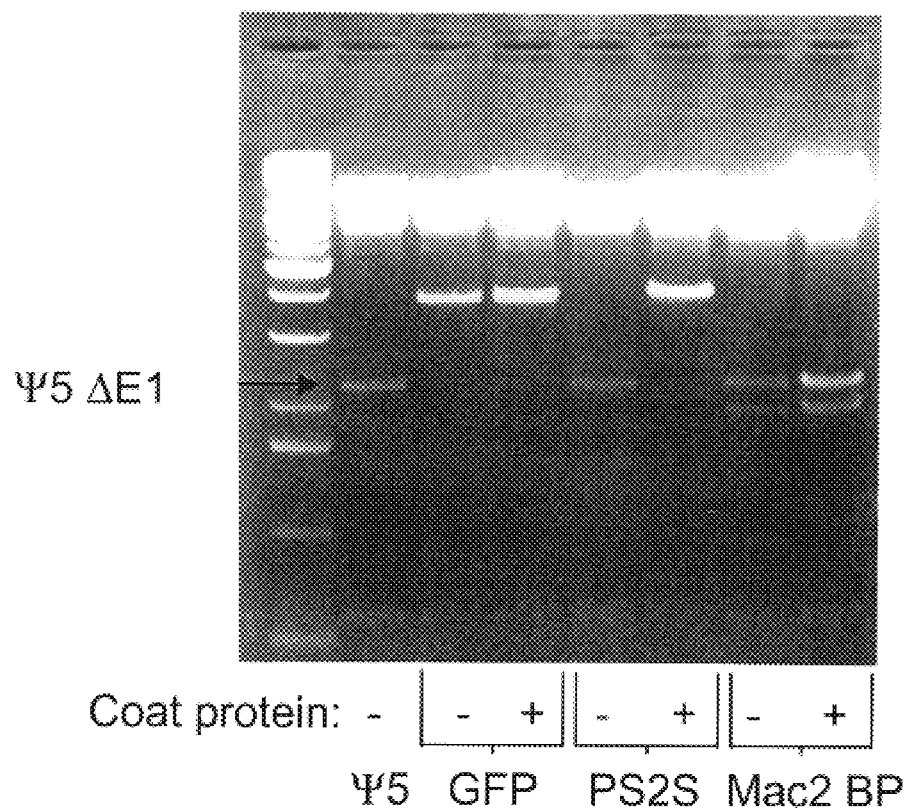
FIGS. 7A through 7C depict DNA restriction analysis of adenovirus vectors created by Cre/lox recombination either with or without transgene suppression. Cre/lox recombination plasmids were co-transfected with Ψ5 adenovirus DNA into either cre8 or CPP cells. DNA was prepared from a either cre8 or CPP cells infected with the virus produced after transfection. Each sample was digested with BsaBI to differentiate between the desired recombinant and Ψ5. The first lane in each panel is a 1kb ladder. The position of the left end band from Ψ5 is marked on the left. Transgene identities are marked at the bottom of each panel, – is cre8 cells and + is CPP cells.
Figure 7B:
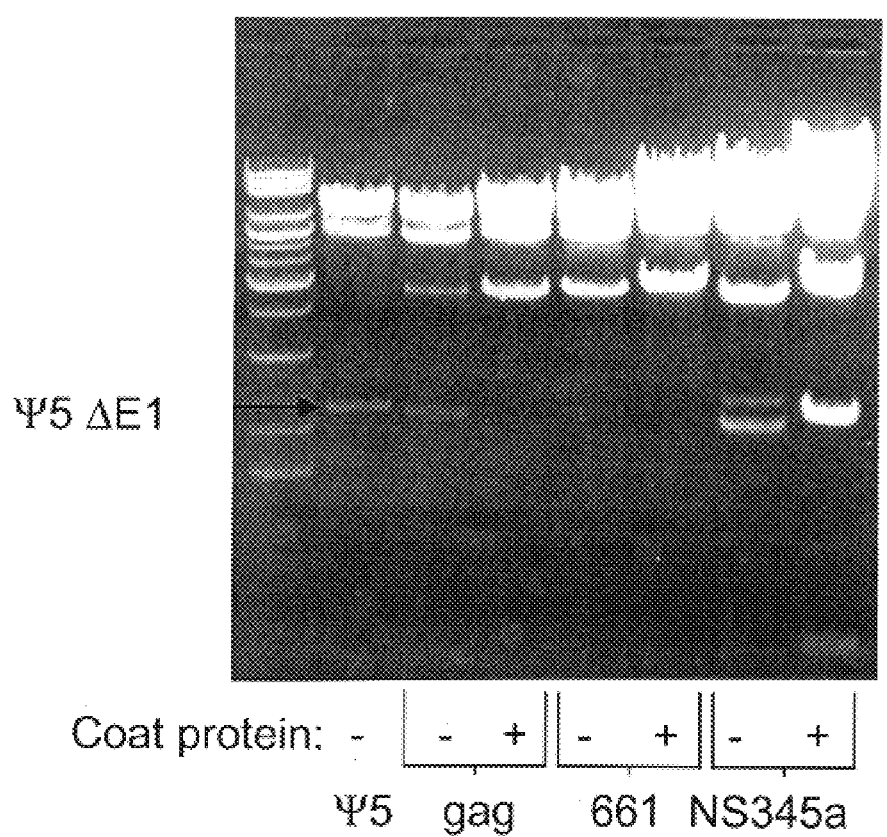
Figure 7C:
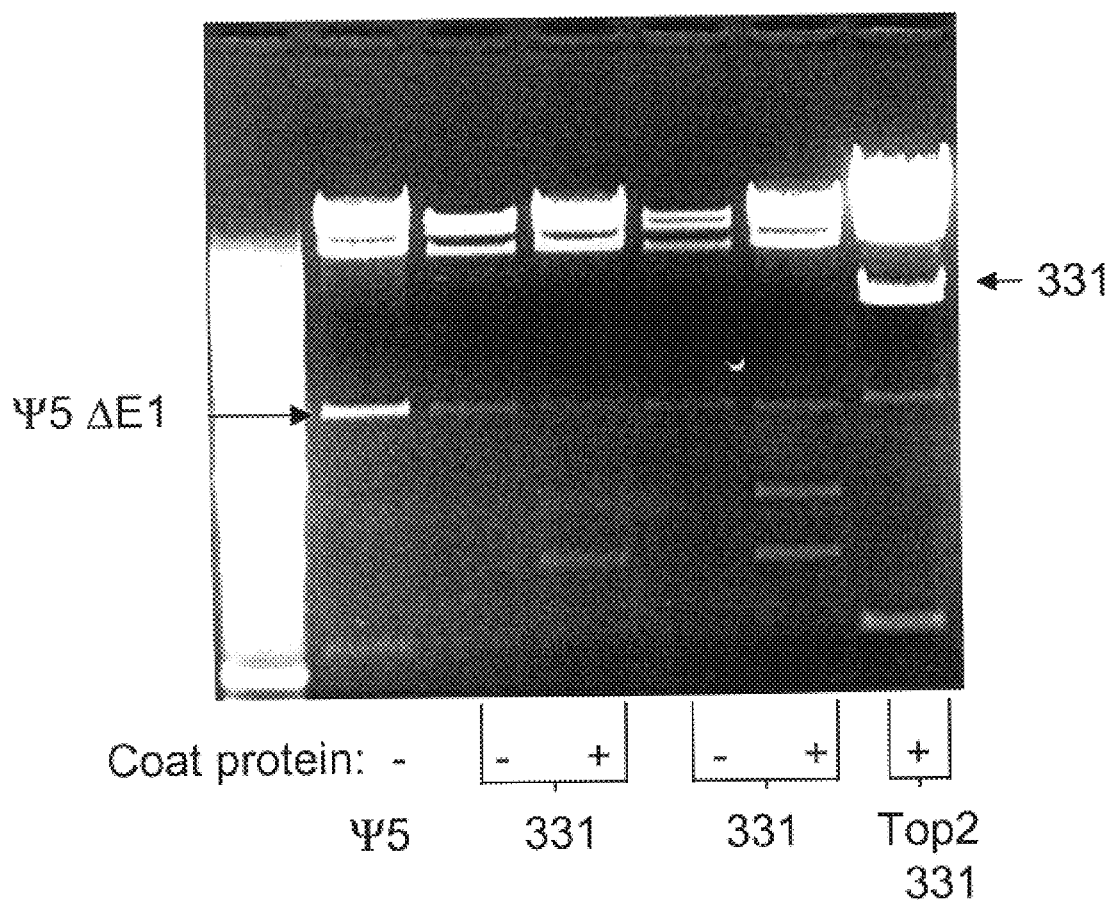

The RNA sequences for the translation operators of these plasmids is shown in FIG. 4 and in the following Table:

A MS2 coat protein expression plasmid was constructed by PCR using the following primers: CCCCTCGAGAC-CATGGCTTCTAACTTTACTC (MS2coatf, SEQ ID NO:19) and GGGGATCCTATTAGTAGATGCCG-GAGTTTG (MS2coatr, SEQ ID NO:20), and then inserting the product into an CMV expression cassette (pBS CP, SEQ ID NO:21).

B. Transient Expression Analyses.

In order to quickly evaluate the expression and suppression of TOP containing constructs, sets of three plasmids were transfected into 6 cm dishes of 293 cells using calcium phosphate (see, e.g., Graham et al. supra). Each set contained 1.5 μg TOP-GFP marker plasmid, 1.5 μg an expression plasmid and 1.5 μg of control plasmid. The expression plasmids were either pBS CP making coat protein or an equivalent plasmid making 16k, an inactive fragment of prolactin. A plasmid making CD25 (PSWIL Rα) was used as a control for transfection efficiency. After 24 hours, the cells were removed with trypsin, stained with PE coupled anti-CD25 (Caltag) and analyzed by FACS for GFP and CD25 intensity.

C. Cells and Viruses.

293 and cre8 (see, e.g., Hardy et al., supra) cells were cultured on Delbecco modified Eagle medium with 10% calf serum. The coat protein expressing cell lines were constructed by co-transfecting pBS CP with pPur (Clontech) into an early passage of cre8 cells. Colonies were selected in puromycin containing growth medium. Candidate cell lines were screened for suppression by infecting each cell line with 400 particles per cell of the TOPGFP virus and comparing the fluorescent intensity to similarly infected cre8 cells at 24 hours post infection. The best cell lines (lowest GFP) were then checked for cre recombinase activity and ability to support E1 deleted viral growth. Thus, a new cell line (called CPP) that expresses MS2 coat protein, cre recombinase and adenovirus E1A and E1B proteins was created.

| Name | Sequence | SEQ ID NO |
|---|---|---|
| MS2 | ACAGAGGAUUACCCAUGU | 4 |
| MS2GFP | CCAUCACCAUCAGGGAUGGU | 5 |
| +4MS2GFP | UCCGACCAUCACCAUCGGGAUGGU | 6 |
| TOPGFP | CAGACCAUCAGGGCUGGAUAUCACCAUG | 7 |
| βutrTOP | ACAUUUGCUUCUAGACACAACUGUGUUCACUACCAGCACC AUCAGGGCUGGGAUAUCAUG | 8 |
| TOP βutrTOP | CAGACCAUCAGGGCUGGAUACAUUUGCUUCUGACACAAC UGUGUUCACUAGCAACCUCAAGUAUACCAUG | 9 |
| TOP2 | CAGACCAUCAGGGCUGGAUAAAUAAAUAAUAGCUGGAGG AUCACCCCAGUACUGUGAACGAUAUCACCAUG | 10 |
| MS2 onsensus | 1 NNNNNRNNANYAN'N'N'N'N'N'N'19 where: N is any base; R is a A or G; Y is C or U; S is C or G; D is A, G or U. Further: bases 1 and 19, 2 and 18, 3 and 17, 4 and 16, 5 and 15, 7 and 14, 8 and 13 base pair. | 17 |
| MS 2 consensus, high affinity | 1 NRNDSASSAN CAS'S'S'N'N'Y'N' 19 where: N is any base; R is an A or G; Y is C or U; S is C or G; D is A, G or U. Further: bases 1 and 19, 2 and 18, 3 and 17, 4 and 16, 5 and 15, 7 and 14, 8 and 13 base pair. | 18 |

The shuttle plasmids to construct adenoviral vectors were based on pTOPPutr. The gene for mac2BP was excised with BamH1, Klenow treated and inserted into Bst II 071 and HpaI sites in pTOPβutr. For hepatitis B surface antigen, HIV p55 gag, and hepatitis C E1/hepatitis B surface antigen fusion protein, genes were inserted between the Bst1071 and SacI sites.

The pTOPβutr plasmid was converted to a E1 deleted adenovirus as detailed in Hardy et al. (1997), supra and a CsC1 purified stock was prepared. To determine if the TOP sequences improved the ability to make new recombinant adenoviruses, shuttle plasmids and Ψ5 DNA were cotransfected into 6 cm dishes of cre8 and CPP. When the infection had spread to all the cells, freeze thaw lysates were made and used to infect a 10 cm dish of the same cell type. After 2 to 3 days, viral DNA was prepared for restriction analysis. Each sample was digested with BsaBI.

All new virions produced the expected recombinant protein products by infection into A549 cells at 1000 particles per cell. Secreted protein was assayed by ELISA on media collected between 16 and 40 hours after infection. Cell associated proteins were assayed from cell lysates also by ELISA.

D. Transgene Suppression Using MS2 Coat Protein.

The MS2 translation operator overlaps the bacterial ribosome binding site and AUG for the replicase protein so that both are shielded by coat protein bound to the RNA. This prevents translation of replicase protein. A eukaryotic version of this arrangement was created by fusing the replicase AUG to start of a GFP marker gene. For the equivalent of a ribosome binding blockade, the $^{m7}$GTP cap structure was positioned at −16 relative to the AUG (MS2GFP, FIG. 4). Without being bound by one theory, it appears that this arrangement makes a very short 5' untranslated region that should be completely covered by a coat protein dimer. Covering the $^{m7}$GTP cap with coat protein should block binding of eIF4E which in turn will prevent ribosome binding in a eukaryotic cell. Additionally, the U at −5 was changed to a C for higher affinity coat protein binding and several other bases were also changed while preserving the overall high affinity binding structure (Schneider et al., supra). The GFP marker gene contains a destabilizing PEST amino acid sequence that decreases the GFP half life to two hours. (see, e.g., Corish et al. (1999) Protein Eng(12):1035–40). This modification insures that the GFP concentration will change quickly as its expression changes. GFP expression was measured by co-transfection into 293 cells and comparing the effect of co-expression of an irrelevant gene to coat protein. The coat protein strongly suppressed fluorescence of MS2GFP but not the dGFP control. A third plasmid expressing CD25 showed equal signal in all transfections. Thus coat protein is able to block expression of genes containing the TOP sequence at their 5' ends.

The unmodified GFP expression from MS2GFP was lower than the control GFP plasmid as one might predict from the short 16 base 5' UTR. Therefore, it was tested whether increasing the length of the 5' UTR would affect basal or suppressed translation by adding sequence either before or after the TOP. The AUG was moved downstream of the TOP by increasing the 5' UTR to 24 and 70 bases (FIG. 4). These changes increased the basal expression substantially while the suppressed expression increased a little. Accordingly, suppression is not linked to having the AUG in the TOP, and is independent of the length of the 5' UTR downstream of TOP over short distances.

A different pattern was observed when nucleotides were inserted upstream of the TOP (FIG. 4). Between about 4 and 30 bases inserted upstream of the TOP increased both basal and suppressed expression. Comparing TOPGFP to +4 MS2GFP and βutrTOP with 0, 4 and 30 nucleotides upstream of the TOP, suppression decreases as 5' UTR upstream of TOP increases.

As a final comparison, the degree of suppression resulting from 2 TOP sequences spaced such that a cooperative interaction could occur by binding 2 dimers of coat protein was tested. Comparing TOP 2 to TOPβutr, the pair of TOP sequences was both very effective at suppression and served as a permissive 5' UTR.

Thus, TOP sequence plus coat protein proved very effective in suppressing transient expression. When TOP was positioned such that the $^{m7}$G cap and the AUG were both shielded by bound coat protein, transgene expression was effectively inhibited by coat protein. In particular, bases added after the TOP, did not decrease the degree of suppression whereas placing 4 bases between the cap and TOP produced a slight increase in GFP with coat protein present, and placing 30 bases in the same position produced a marked increase in GFP with coat protein present.

E. Suppression in a Coat Protein Cell Line.

TOPGFP and dGFP plasmids were converted into adenoviral vectors to allow screening of candidate cell lines and monitor the degree of suppression at all stages of the viral life cycle. Stable cell lines were made by co-transfecting coat protein expression and puromycin resistance plasmids into cre8 cells. Such cells should have a constant source of coat protein during adenoviral vector recombination and growth. The resulting cell line was called CPP, was 293-based and expresses both cre recombinase and coat protein.

Next the degree of suppression at early and late times after infection was determined (FIG. 6). Both cre8 and CPP cells were infected with dGFP and TOPGFP virus and then analyzed the fluorescent intensity at 6, 18, 24, and 48 hours. Expression and suppression were maximal at the 24 hour time point. One possible explanation of this finding is that GFP mRNA concentration is becoming very high since there are now many genomes transcribing RNA, and the RNA's made from viral genomes are transported out to the cytoplasm while cellular RNA is blocked in the nucleus. The more effective suppression results from the decrease in the concentration of phosphorylated eIF4E allowing coat protein to compete more effectively.

F. Suppression Improves Virion Stability.

Previously, it has been found that highly processed membrane proteins were difficult to insert into adenoviral vectors by cre/lox recombination. Therefore several genes that have potential processing or assembly problems were tested including: hepatitis B surface antigen (PS2S), HIV p55 gag (gag), a hepatitis C E1/hepatitis B surface antigen fusion protein (330), a hepatitis C E2/hepatitis B surface antigen fusion (661S), a mac2 binding protein (mac2BP) and hepatitis C non-structural proteins NS345a (NS345a). Each gene was inserted into an adenovirus shuttle plasmid such that each mRNA would begin with TOPβutr (also TOP2 for 330S), and vectors assembled in either cre8 or CPP cells. In this procedure, cre recombinase recombines the donor virus Ψ5 with the shuttle plasmid to produce a new adenovirus vector. While the Ψ5 virus can grow in cre8 cells, cre recombinase strongly selects against Ψ5 by deleting the packaging sequence, giving recombinants a sizable growth advantage that ordinarily allows them to take over the culture. However, if the transgene protein interferes with viral growth the grow advantage will be decreased. In such cases anywhere from pure Ψ5 to a mixture of the recombinant and Ψ5 was recovered depending on the gene. To assess the yield of recombinant and Ψ5, vector DNA was prepared a diagnostic restriction analysis was done. As a control a GFP shuttle plasmid lacking the TOP sequence was included.

The GFP plasmid was efficiently converted to GFP virus in both cell lines (FIG. 6). The other transgenes caused varying degrees of difficulty in cre8 cells. The most extreme example was 330 where it was seen that linkage to TOP2 was essential. Recombination using 330 linked to TOP2 made the expected recombinant in CPP cells. In contrast, Ψ5 or aberrant fragments were recovered from cre8 and CPP cells using 330 linked to TOPβutr. Since the 330 protein seems to cause severe problems, we were concerned that the TOP2 330 vector might have been selected to carry a nonfunctional gene. The TOP2 330 vector was checked by infecting A549 cells, a human cell line that infects well with adenovirus but will not support the growth of E1 deleted vectors and also lacks the MS2 coat protein. These infected cells produced a high level of fusion protein that reacted simultaneously with HBV surface antigen and HCV E1 antibodies.

For HBV sAg (PS2S), only Ψ5 virus were recovered in cre8 cells, while the PS2S recombinant was the overwhelming product in CPP cells. For mac2 BP, a new virus was generated on both cell types, however in cre8 cells the recombinant virus and Ψ5 were equal in concentration, and there were several fragments of anomalous size probably resulting from deletions. In contrast, the predicted mac2 BP fragment predominated in CPP cells. For p55 gag, more virus was recovered on the CPP cells than cre8 and the same was seen with NS345a.

Thus, the combination of the bacteriophage MS2 coat protein and its RNA binding sequence can function to increase the success rate in making new adenoviral vectors. Using this combination method, new vectors (virions) that had proved difficult to make by others methods were produced.

Example 2

Suppression of Transgene Expression in Alphavirus

The RNA binding site for bacteriophage R17 coat protein (Krug et al. 1982, *Biochemistry* 21:4713–4720) can be introduced in the 5' end of the subgenomic RNA. The minimal R17 binding site comprises a sequence AAACAUGAGGAUUACCCAUGU (SEQ ID NO:1) and forms a stem loop structure absolutely required for binding. Analysis of a population of high affinity RNA ligands to the coat protein revealed the components of a hairpin that promote favorable interactions with the coat protein (Schneider et al. 1992 *J. Mol. Biol.* 228:862–869).

To demonstrate the ability of this binding site to reduce the transgene expression from alphavirus vectors in the presence of the R17 coat protein, variants of the binding site were introduced into the 5'-nontranslated (NTR) region of a Sindbis vector subgenomic RNA, immediately upstream of the AUG initiator codon for a reporter gene. Additional vectors containing other transgenes may be readily constructed in a similar manner by one of skill in the art using the teachings provided herein.

Two binding sites were designed to include components essential for both high affinity binding to the coat protein and high efficiency of replication and subgenomic transcription of the Sindbis virus derived vectors. In both binding sites, specific elements were introduced comprising: 1) in the loop, a C replaced $U_{13}$ to maximize functionality (e.g., increase binding affinity) of this structure in eukaryotic cells, and 2) the two pairs $G_9$-$C_{16}$, $G_{10}$-$C_{15}$ were inverted. Furthermore, one binding site also included 1) the substitution of the pair $U_6$-$A_{18}$ into G-C in the stem loop to eliminate the AUG codon, and 2) the substitution of $A_1A_2$ with first 5 nucleotides (AUAGU) of Sindbis 5'-nontranslated region which are essential for subgenomic transcription. This binding site was named 5TOP. The other binding site was designed to include the first 5 nucleotides of Sindbis 5'-nontranslated region in the stem, resulting in the substitution of the pairs $A_3$-$U_{21}$, $C_4$-$G_{20}$, $A_5$-$U_{19}$, and $G_7C_{17}$ with the pairs U-A, A-U, G-C, and C-G respectively. This binding site was named TOP.

Introduction of the 5TOP binding site was accomplished by PCR amplification of two overlapping fragments also generated by PCR amplification, as follows:

5TOPF:
5'-CAGCACCATCAGGGCTGGCAGCATAGTACATTTCATCTGAC (SEQ ID NO:22)

SCG812OR:
5'-CGTTGTGGCTGTTGTAGTTGTAC (SEQ ID NO:23)

In the forward primer (5TOPF), bases 1–19 are the R17 coat protein-binding site, while bases 20–42 are complementary to nucleotides 7603–7625 of the Sindbis replicon vector expressing a GFP reporter (SINCR-GFP). The reverse primer is complementary to nucleotides 8105–8083 of the same vector.

The second fragment was amplified using the following two oligonucleotides:

SCR728F:
5'-TGCGGCGGATTTATCTTGCAAG (SEQ ID NO:24)

5TOPR:
5'-CAGCCCTGATGGTGCTGGACTATTTAGGACCACCGTAGAG (SEQ ID NO:25)

The forward primer is complementary to the 7281–7302 nucleotides of the Sindbis GFP reporter vector, while the reverse primer contains the R17 coat protein binding site in nucleotides 1–19, and nucleotides 20–41 are complementary to 7581–7602 of the Sindbis vector. The oligonucleotides were used at 2 μM concentration with 0.1 μg of plasmid template in a single, 10-cycle PCR reaction with Pfu Polymerase, as suggested by the supplier. The amplification protocol is shown below.

| Temperature (° C.) | Time (Min.) | No. Cycles |
| --- | --- | --- |
| 94 | 2 | 1 |
| 94 | 0.5 | |
| 60 | 0.5 | 10 |
| 72 | 2 | |

The two amplified fragments were purified from an agarose gel using a QIAquick gel extraction kit, and an aliquot of each fragment was used as template for a second PCR amplification. The two fragments were mixed with Vent Polymerase as suggested by supplier, and one PCR amplification cycle was performed:

| Temperature (° C.) | Time (Min.) | No. Cycles |
| --- | --- | --- |
| 94 | 2 | 1 |
| 94 | 0.5 | |
| 42 | 1 | 1 |
| 72 | 3 | |

The following primers, overlapping respectively with the $BamHI_{7335}$ and XhoI sites of the Sindbis replicon, then were added at a 2 μM concentration:

SCR7320F:
5' ATATATGCGTGCCGCGTGGCGGATCCCC (SEQ ID NO:26)

SCRG7672R:
5' ATATATCATGGTGGCTCGAGGGTGGTGTT (SEQ ID NO:27)

PCR amplification was performed as follows:

| Temperature (° C.) | Time (Min.) | No. Cycles |
|---|---|---|
| 94 | 2 | 1 |
| 94 | 0.5 | |
| 60 | 0.5 | 30 |
| 72 | 2 | |

The PCR product (300 bp) was purified using the QIAquick kit, digested with BamHI and XhoI, gel purified from agarose gel as described above, and ligated into plasmid SINCR-GFP that had also been digested with BamHI and XhoI and purified from an agarose gel. Clones containing the inserts were verified by sequencing and, finally, the $BamHI_{4634}$-$BamHI_{7355}$ was reinserted into this construct. The new Sindbis virus vector construct was designated SINCR-5TOP-GFP.

The second Sindbis derived vector was constructed in a similar manner, with the only differences being the forward oligonucleotide primer for the PCR amplification of the first fragment, as follows:

TOPF:
5' CACCATCAGGGACTACAGCATAGTACATT TCATCTGAC (SEQ ID NO:28) and, the reverse primer for the PCR amplification of the second fragment, as follows:

TOPR:
5' TAGTCCCTGATGGTGACTATTTAGGACC ACCGTAGAG (SEQ ID NO:29)

Following insertion of the overlapping PCR fragment into the SINCR-GFP vector, this new Sindbis replicon construct was designated SINCR-TOP-GFP.

Next, the ability of these new vectors to express the reporter gene GFP and to be packaged into vector particles was demonstrated. Plasmid DNA from these two new constructs and from the parental construct were linearized and used for in vitro transcription as described previously. Each transcript was co-transfected into BHK cells with together with helper RNAs expressing capsid and glycoproteins (Polo et al., 1999, ibid). Transfected cells were incubated for 24 hr, at which time the culture supernatants were collected and the cells harvested. The harvested cells were analyzed by flow cytometry. The supernatants were clarified by centrifugation, serially diluted and used to infect in duplicate, naive BHK-21 cells for approximately 14 hr. The infected cells were counted based on GFP fluorescence to determine vector particle titer in the original supernatants. Both constructs efficiently expressed GFP reporter and were packaged into recombinant alphavirus vector particles.

To demonstrate that transgene expression can be downregulated in the presence of R17 coat protein, vector particles derived from both modified constructs, as well as the parental construct, were used to infect at an MOI=3, 293 cells and 293 derivative cells that express the R17 coat protein. Following incubation for 24 hrs, GFP expression was analyzed by flow cytometry. As shown in FIG. 2, expression of the GFP transgene was reduced significantly in R17-expressing cells (as compared to 293 cells) for each of the modified vector replicons, but not for the wild-type SINCR replicon. The R17 coat protein similarly may be expressed in a variety of cell lines for use in the packaging of alphavirus vector particles, and established methods for packaging are provided elsewhere (U.S. Pat. No. 5,789,245, Dubensky et al, 1996, ibid; Polo et al., 1999, ibid) These data demonstrate the ability to specifically down-regulate transgene expression from alphavirus vectors, using methods of the present invention.

Example 3

Suppression of Transgene Expression and Production of AAV Virions

To suppress transgene toxicity during recombinant AAV virion (rAAV) production two components are used: a TOP in the AAV vector and MS2 coat protein in the packaging cell. The TOP sequence is included in the AAV vector essentially as described in Examples 1 and 2 for adenovirus and alphavirus vectors. Thus, the AAV vector has the following sequences: an AAV inverted terminal repeat (ITR), a promoter driving mRNA for the transgene, a high affinity Top sequence at the 5' end of the mRNA, a transgene, a polyadenylation signal, and a $2^{nd}$ ITR (see, also FIG. 8). Optionally, an intron is included in the vector and can be inserted anywhere in the transgene mRNA 3' of the TOP sequence. For optimal suppression, there is no untranslated sequence on the 5' side of the TOP. For maximal expression, the Top is followed by a short untranslated sequence located between the Top and the AUG.

The rAAV virions are packaged in a suitable cell line, for example, 293, HeLa, CV1 and KB. The coat protein is produced constitutively or transiently. Constitutive expression of the coat protein is obtained from the CPP cell line as described above for adenovirus. Briefly, CPP is co-transfected with an AAV packaging plasmid containing rep and cap but no ITR's, or with 2 plasmids containing rep on one and cap on the other; plus a rAAV vector plasmid with a TOP, and a third plasmid containing the helper functions for AAV growth. After 3 days the packaged virions are released from the cells. Alternatively, the helper functions can be provided by a helper virus such as adenovirus or herpes virus.

Transient transfection techniques are also used to supply the coat protein, for example, by including an expression plasmid to make coat protein in addition the TOP rAAV vector plasmid, packaging plasmid(s) and helper functions. rAAV virions are produced from stable packaging cell lines. As noted above, the packaging cell line can constitutively express MS2 coat protein and can be made by standard techniques of transfection followed by selection starting with a rAAV packaging cell line. The rAAV genome is carried on and introduced into the cell line on a plasmid, as a packaged rAAV, or on an adenovirus. In the adenovirus case, rAAV genome is inserted into the E1 or E3 regions of the virus by standard techniques. Since the transgene carried in the rAAV may have a negative effect on production of such a carrier adenovirus vector, the adenovirus vector is packaged using a coat protein expressing cell line such as CPP.

Example 4

Suppression of Transgene Expression in Retrovirus Vectors

Figure 9A:
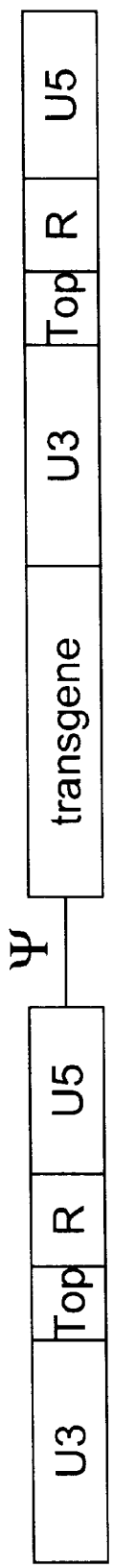
FIGS. 9A and 9B are schematics depicting retroviral vectors having TOP sequences.
Figure 9A:
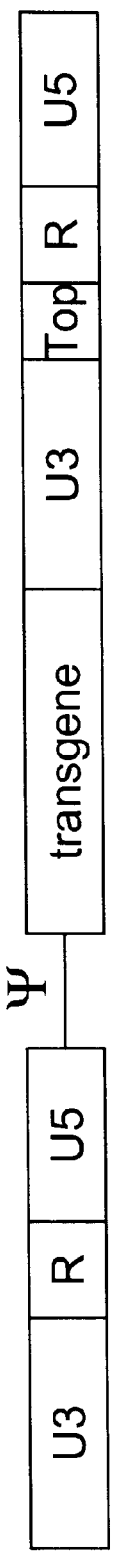

Transgene expression (e.g., translation) is suppressed during retrovirus virion production using a modified retrovirus vector and a source of MS2 coat protein. The location of the TOP in the vector depends on the template for the retrovirus vector. If the retroviral vector is produced from a plasmid (either transiently or integrated into a packaging cell line) then the Top is placed at the 5' end of both long terminal repeat (LTR) "R" sequences (see, FIG. 9A). The resulting polynucleotides have an expanded R sequence. If packaging is accomplished by transient transfection, then the coat protein is provided on a plasmid and co-transfected along with the vector plasmid and the packaging plasmids. If a packaging cell line is used then the cell line expresses a coat protein constitutively. Alternatively, if the integrated copies of the retrovirus vector are derived from infecting virus rather than DNA, then the TOP sequence is located at the 5' end of the 3' R region (see, FIG. 9A). During replication the TOP sequence will be added to the 5' LTR.

Example 5

Self Inactivating Retrovirus or Lentivirus Vectors

Figure 9B:

For lentivirus vectors (see, e.g., Naldini et al. (1996) *Science* 272(5259):263–267) and self inactivating (Sin) vectors (see, e.g., Julius et al. (2000) *Biotechniques* 28(4): 702–708; Yu et al. (1986) *Proc Natl Acad Sci USA* 83(10): 3194–3198), an internal promoter is used to drive the transgene mRNA. The TOP sequence is located after the internal promoter at the 5' end of the transgene RNA (see, FIG. 9B). These constructs are assembled in plasmids using standard techniques. As in Example 4, if the vector is made by transient transfection, then the coat protein is supplied from an expression plasmid. Alternatively, the coat protein can be supplied from a stable integrated coat protein gene. For vector production from packaging cell lines the coat protein is made from an integrated gene.

While the present invention has been described above both generally and in terms of preferred embodiments, it is understood that variations and modifications will occur to those skilled in the art in light of the description, supra. Therefore, it is intended that the appended claims cover all such variations coming within the scope of the invention as claimed.

What is claimed is:

1. A host cell comprising a translational operator sequence (TOP)-binding ligand and packaging elements necessary for the production of infectious recombinant virus, wherein the TOP-binding ligand is selected from the group consisting of MS2 coat proteins, bacteriophage R17 coat proteins, tobramycin antibiotic and Hoechst dyes.

2. The host cell of claim 1, wherein the TOP-binding ligand is encoded by a nucleic acid molecule.

3. The host cell of claim 1 or claim 2, wherein the packaging elements are encoded by one or more polynucleotides.

4. The host cell of claim 1, wherein the TOP-binding ligand comprises an MS2 or R17 coat protein.

5. The host cell of claim 1, further comprising a cre recombinase.

6. The host cell of claim 1, wherein the packaging elements comprise E1A and E1B.

7. The host cell of claim 1, wherein the host cell is a 293 cell.

8. The host cell of claim 3, wherein the host cell is stably or transiently transfected with the nucleic acid molecule encoding the TOP-binding ligand and stably or transiently transfected with the polynucleotides encoding the packaging elements.

9. The host cell of claim 8, wherein the TOP-binding ligand comprises an MS2 or R17 coat protein.

10. A method of producing recombinant virions comprising culturing a recombinant viral vector comprising a MS2 translational operator sequence (TOP) that includes an mRNA $^{m7}$G-cap sequence, and wherein the TOP sequence is operably linked to a transgene, with (i) a TOP-binding ligand selected from the group consisting of MS2 coat proteins, bacteriophage R17 coat proteins, tobramycin antibiotic and Hoechst dyes and (ii) packaging elements necessary for the production of infectious recombinant virus; under conditions such that expression of the transgene is suppressed during production of the virions.

11. The method of claim 10, wherein the TOP-binding ligand is an MS2 coat protein.

12. The method of claim 10, wherein the TOP-binding ligand is an R17 coat protein.

13. The method of claim 10, wherein the TOP-binding ligand is encoded by a polynucleotide stably or transiently transfected into a host cell.

14. The method of claim 10, wherein the TOP is located within about 30 base pairs of the mRNA $^{m7}$G-cap sequence.

15. The method of claim 10, wherein the recombinant viral vector is an adenoviral vector.

16. The method of claim 10, wherein the recombinant viral vector is an alphaviral vector.

17. The method of claim 10, wherein the recombinant viral vector is a retroviral vector.

18. The method of claim 10, wherein the recombinant viral vector is an adeno- associated viral vector.

19. The method of claim 13, wherein the packaging elements are encoded by one or more polynucleotides stably or transiently transfected into the host cell.

20. The method of claim 19, wherein the host cell comprises a 293 cell line expressing MS2 coat protein, an E1A protein and an E1B protein.

21. The method of claim 15, further comprising culturing the recombinant adenoviral vector and the packaging elements in the presence of an E1, E3 deleted adenovirus construct having loxP sites flanking the packaging site and a cre recombinase.

22. The method of claim 15, wherein the TOP sequence is derived from an MS2 bacteriophage sequence and the TOP-binding ligand is an MS2 or R17 coat protein.

23. The method of claim 15, wherein the TOP is located within about 60 base pairs of the mRNA $^{m7}$G-cap sequence.

24. The method of claim 15, wherein the TOP is located within about 30 base pairs of the mRNA $^{m7}$G-cap sequence.

25. The method of claim 15, wherein a 293 cell line expressing an MS2 coat protein, a cre recombinase, an E1A protein and E1B protein is used.

26. The method of claim 17, wherein the retrovirus is a lentivirus.

27. The method of claim 26, wherein the lentivirus is selected from the group consisting of feline immunodeficiency virus (FIV), human immunodeficiency virus (HIV), human immunodeficiency virus-1 (HIV-1), human immunodeficiency virus-2 (HIV-2) and simian immunodeficiency virus (SIV).

28. A viral vector comprising a transgene operably linked to a TOP sequence derived from an MS2 or R17 bacteriophage sequence.

29. The viral vector of claim 28, wherein the viral vector an adenoviral vector.

30. The viral vector of claim 28, wherein the viral vector is an alphaviral vector.

31. The viral vector of claim 28, wherein the viral vector is a retroviral vector.

32. The viral vector of claim 31, wherein the retrovirus is a lentivirus.

33. The viral vector of claim 28, wherein the viral vector is an adeno-associated viral vector.

* * * * *

SEQUENCE LISTING

<160> NUMBER OF SEQ ID NOS: 29

<210> SEQ ID NO 1
<211> LENGTH: 21
<212> TYPE: RNA
<213> ORGANISM: Bacteriophage MS2

<400> SEQUENCE: 1
aaacaugagg auuacccaug u                                             21

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: 5TOP

<400> SEQUENCE: 2
auaguccagc accaucaggg cugg                                          24

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: TOP

<400> SEQUENCE: 3
auagucacca ucagggacua                                               20

<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: MS2b

<400> SEQUENCE: 4
acagaggauu acccaugu                                                 18

<210> SEQ ID NO 5
<211> LENGTH: 20
<212> TYPE: RNA
<213> ORGANISM: Artificial Sequence

```
<220> FEATURE:
<223> OTHER INFORMATION: Description of Artificial Sequence: MS2GFP

<400> SEQUENCE: 5
ccaucaccau cagggauggu                                                    20

<210> SEQ ID NO 6
<211> LENGTH: 24
<212> TYPE: RNA
<213> ORGANISM: Artificial Sequence
<220> FEATURE:
<223> OTHER INFORMATION: Description of Artificial Sequence: +4MS2GFP

<400> SEQUENCE: 6
uccgaccauc accaucggga uggu                                               24

<210> SEQ ID NO 7
<211> LENGTH: 28
<212> TYPE: RNA
<213> ORGANISM: Artificial Sequence
<220> FEATURE:
<223> OTHER INFORMATION: Description of Artificial Sequence: TOPGFP

<400> SEQUENCE: 7
cagaccauca gggcuggaua ucaccaug                                           28

<210> SEQ ID NO 8
<211> LENGTH: 60
<212> TYPE: RNA
<213> ORGANISM: Artificial Sequence
<220> FEATURE:
<223> OTHER INFORMATION: Description of Artificial Sequence: Beta
      utrTOP

<400> SEQUENCE: 8
acauuugcuu cuagacacaa cuguguucac uaccagcacc aucagggcug ggauaucaug        60

<210> SEQ ID NO 9
<211> LENGTH: 70
<212> TYPE: RNA
<213> ORGANISM: Artificial Sequence
<220> FEATURE:
<223> OTHER INFORMATION: Description of Artificial Sequence: TOP Beta
      utr

<400> SEQUENCE: 9
cagaccauca gggcuggaua cauuugcuuc ugacacaacu guucacua gcaaccucaa         60 guauaccaug                                                               70

<210> SEQ ID NO 10
<211> LENGTH: 71
<212> TYPE: RNA
<213> ORGANISM: Artificial Sequence
<220> FEATURE:
<223> OTHER INFORMATION: Description of Artificial Sequence: TOP2

<400> SEQUENCE: 10
cagaccauca gggcuggaua aauaaauaau agcuggagga ucaccccagu acugugaacg       60 auauccauu g                                                              71

<210> SEQ ID NO 11
<211> LENGTH: 77
<212> TYPE: DNA
<213> ORGANISM: Artificial Sequence
<220> FEATURE:
```

<223> OTHER INFORMATION: Description of Artificial Sequence: primer GFPF

<400> SEQUENCE: 11
ctggtttagg gatccgacca tcaccatcag ggatggtgag caagggcgag gagctcttca    60
ccggggtggt gcccatc    77

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer GFPR

<400> SEQUENCE: 12
gggaattctt actacacatt gatcctagca g    31

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: primer topa

<400> SEQUENCE: 13
gatccgacca gcaccatcag ggctgggata tcaccatggt gagcaagggc gaggagct    58

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: primer topb

<400> SEQUENCE: 14
gatccgacat ttgcttctag acacaactgt gttcactacc agcaccatca gggctgggat    60

<210> SEQ ID NO 15
<211> LENGTH: 71
<212> TYPE: DNA
<213> ORGANISM: Artificial Sequence
<220> FEATURE:
<223> OTHER INFORMATION: Description of Artificial Sequence: primer top
    Beta a

<400> SEQUENCE: 15
acatttgctt ctgacacaac tgtgttcact agcaacctca agtataccat ggtgagcaag    60
ggcgaggagc t    71

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: primer top
    Beta b

<400> SEQUENCE: 16
aaataaataa tagctggagg atcaccccag tactgtgaac gat    43

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: MS2

-continued

```
       consensus
<221> NAME/KEY: misc_feature
<222> LOCATION: (1)..(19)
<223> OTHER INFORMATION: where N represents an A or G or U or C

<400> SEQUENCE: 17
nnnnnrnnan yannnnnn                                               19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: MS2 high
      affinity
<221> NAME/KEY: misc_feature
<222> LOCATION: (1)..(19)
<223> OTHER INFORMATION: where N represents an A or G or U or C

<400> SEQUENCE: 18
nrndsassan casssnnyn                                              19

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: primer
      MS2coatf

<400> SEQUENCE: 19
cccctcgaga ccatggcttc taactttact c                                31

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: primer
      MS2coatr

<400> SEQUENCE: 20
ggggatccta ttagtagatg ccggagtttg                                  30

<210> SEQ ID NO 21
<211> LENGTH: 4883
<212> TYPE: DNA
<213> ORGANISM: Artificial Sequence
<220> FEATURE:
<223> OTHER INFORMATION: Description of Artificial Sequence: pBS CP

<400> SEQUENCE: 21
ctgcaggtcg actctagagg atccggcctc ggcctctgca taaataaaaa aaattagtca      60
gccatgagct tggcccattg catacgttgt atccatatca taatatgtac atttatattg     120
gctcatgtcc aacattaccg ccatgttgac attgattatt gactagttat taatagtaat     180
caattacggg gtcattagtt catagcccat atatggagtt ccgcgttaca taacttacgg     240
taaatggccc gcctggctga ccgcccaacg acccccgccc attgacgtca ataatgacgt     300
atgttcccat agtaacgcca atagggactt tccattgacg tcaatgggtg gagtatttac     360
ggtaaactgc ccacttggca gtacatcaag tgtatcatat gccaagtacg ccccctattg     420
acgtcaatga cggtaaatgg cccgcctggc attatgccca gtacatgacc ttatgggact     480
ttcctacttg gcagtacatc tacgtattag tcatcgctat taccatggtg atgcggtttt     540
```

```
ggcagtacat caatgggcgt ggatagcggt ttgactcacg gggatttcca agtctccacc    600
ccattgacgt caatgggagt ttgttttggc accaaaatca acgggacttt ccaaaatgtc    660
gtaacaactc cgccccattg acgcaaatgg gcggtaggcg tgtacggtgg gaggtctata    720
taagcagagc tcgtttagtg aaccgtcaga tcgcctggag acgccatcca cgctgttttg    780
acctccatag aagacaccgg gaccgatcca gcctcccctc gaagcttaca tgtggtaccg    840
agctcggatc ctgagaactt cagggtgagt ctatgggacc cttgatgttt tctttcccct    900
tcttttctat ggttaagttc atgtcatagg aaggggagaa gtaacagggt acacatattg    960
accaaatcag ggtaattttg catttgtaat tttaaaaaat gctttcttct tttaatatac   1020
ttttttgttt atcttatttc taatactttc cctaatctct ttctttcagg caataatga    1080
tacaatgtat catgcctctt tgcaccattc taaagaataa cagtgataat ttctgggtta   1140
aggcaatagc aatatttctg catataaata tttctgcata taaattgtaa ctgatgtaag   1200
aggtttcata ttgctaatag cagctacaat ccagctacca ttctgctttt attttatggt   1260
tgggataagg ctggattatt ctgagtccaa gctaggccct tttgctaatc atgttcatac   1320
ctcttatctt cctcccacag ctcctgggca acgtgctggt ctgtgtgctg gcccatcact   1380
ttggcaaaga attgatcccc ccctcgagac catggcttct aactttactc agttcgttct   1440
cgtcgacaat ggcggaactg cgacgtgac tgtcgcccca agcaacttcg ctaacggggt   1500
cgctgaatgg atcagctcta actcgcgttc acaggcttac aaagtaacct gtagcgttcg   1560
tcagagctct gcgcagaatc gcaaatacac catcaaagtc gaggtgccta aagtggcaac   1620
ccagactgtt ggtggtgtag agcttcctgt agccgcatgg cgttcgtact taaatatgga   1680
actaaccatt ccaattttcg ctacgaattc cgactgcgag cttattgtta aggcaatgca   1740
aggtctccta aaagatggaa acccgattcc ctcagcaatc gcagcaaact ccggcatcta   1800
ctaataggat ccccaacttg tttattgcag cttataatgg ttacaaataa agcaatagca   1860
tcacaaattt cacaaataaa gcattttttt cactgcattc tagttgtggt ttgtccaaac   1920
tcatcaatgt atcttatcat gtctggatca tcgataccgt cgacctcgag ggggggcccg   1980
gtacccaatt cgccctatag tgagtcgtat tacaattcac tggccgtcgt tttacaacgt   2040
cgtgactggg aaaaccctgg cgttacccaa cttaatcgcc ttgcagcaca tccccctttc   2100
gccagctggc gtaatagcga agaggcccgc accgatcgcc cttcccaaca gttgcgcagc   2160
ctgaatggcg aatgggacgc gccctgtagc ggcgcattaa gcgcggcggg tgtggtggtt   2220
acgcgcagcg tgaccgctac acttgccagc gccctagcgc ccgctccttt cgctttcttc   2280
ccttcctttc tcgccacgtt cgccggcttt ccccgtcaag ctctaaatcg ggggctccct   2340
ttagggttcc gatttagtgc tttacggcac ctcgacccca aaaaacttga ttagggtgat   2400
ggttcacgta gtgggccatc gccctgatag acggtttttc gccctttgac gttggagtcc   2460
acgttcttta atagtggact cttgttccaa actggaacaa cactcaaccc tatctcggtc   2520
tattcttttg atttataagg gattttgccg atttcggcct attggttaaa aaatgagctg   2580
atttaacaaa aatttaacgc gaattttaac aaaatattaa cgcttacaat ttaggtggca   2640
cttttcgggg aaatgtgcgc ggaacccta tttgtttatt tttctaaata cattcaaata   2700
tgtatccgct catgagacaa taaccctgat aaatgcttca ataatattga aaaggaaga   2760
gtatgagtat tcaacatttc cgtgtcgccc ttattccctt ttttgcggca ttttgccttc   2820
ctgttttttgc tcacccagaa acgctggtga agtaaaagat gctgaagat cagttgggtg   2880
cacgagtggg ttacatcgaa ctggatctca acagcggtaa gatccttgag agttttcgcc   2940
```

```
ccgaagaacg tttttccaatg atgagcactt ttaaagttct gctatgtggc gcggtattat   3000
cccgtattga cgccgggcaa gagcaactcg gtcgccgcat acactattct cagaatgact   3060
tggttgagta ctcaccagtc acagaaaagc atcttacgga tggcatgaca gtaagagaat   3120
tatgcagtgc tgccataacc atgagtgata acactgcggc caacttactt ctgacaacga   3180
tcggaggacc gaaggagcta accgcttttt tgcacaacat gggggatcat gtaactcgcc   3240
ttgatcgttg ggaaccggag ctgaatgaag ccataccaaa cgacgagcgt gacaccacga   3300
tgcctgtagc aatggcaaca acgttgcgca aactattaac tggcgaacta cttactctag   3360
cttcccggca acaattaata gactggatgg aggcggataa agttgcagga ccacttctgc   3420
gctcggccct tccggctggc tggtttattg ctgataaatc tggagccggt gagcgtgggt   3480
ctcgcggtat cattgcagca ctggggccag atggtaagcc ctcccgtatc gtagttatct   3540
acacgacggg gagtcaggca actatggatg aacgaaatag acagatcgct gagataggtg   3600
cctcactgat taagcattgg taactgtcag accaagttta ctcatatata ctttagattg   3660
atttaaaact tcattttaa tttaaaagga tctaggtgaa gatcctttt gataatctca   3720 tgaccaaaat cccttaacgt gagttttcgt tccactgagc gtcagacccc gtagaaaaga   3780
tcaaaggatc ttcttgagat cctttttttc tgcgcgtaat ctgctgcttg caaacaaaaa   3840
aaccaccgct accagcggtg gtttgtttgc cggatcaaga gctaccaact cttttccga   3900 aggtaactgg cttcagcaga gcgcagatac caaatactgt ccttctagtg tagccgtagt   3960
taggccacca cttcaagaac tctgtagcac cgcctacata cctcgctctg ctaatcctgt   4020
taccagtggc tgctgccagt ggcgataagt cgtgtcttac cgggttggac tcaagacgat   4080
agttaccgga taaggcgcag cggtcgggct gaacggggg ttcgtgcaca cagcccagct   4140
tggagcgaac gacctacacc gaactgagat acctacagcg tgagctatga gaaagcgcca   4200
cgcttcccga agggagaaag gcggacaggt atccggtaag cggcagggtc ggaacaggag   4260
agcgcacgag ggagcttcca gggggaaacg cctggtatct ttatagtcct gtcgggtttc   4320
gccacctctg acttgagcgt cgatttttgt gatgctcgtc aggggggcgg agcctatgga   4380
aaaacgccag caacgcggcc tttttacggt tcctggcctt ttgctggcct tttgctcaca   4440
tgttctttcc tgcgttatcc cctgattctg tggataaccg tattaccgcc tttgagtgag   4500
ctgataccgc tcgccgcagc cgaacgaccg agcgcagcga gtcagtgagc gaggaagcgg   4560
aagagcgccc aatacgcaaa ccgcctctcc ccgcgcgttg gccgattcat taatgcagct   4620
ggcacgacag gtttcccgac tggaaagcgg gcagtgagcg caacgcaatt aatgtgagtt   4680
agctcactca ttaggcaccc caggctttac actttatgct tccggctcgt atgttgtgtg   4740
gaattgtgag cggataacaa tttcacacag gaaacagcta tgaccatgat tacgccaagc   4800
tcgaaattaa ccctcactaa agggaacaaa agctggagct ccaccgcggt ggcggccgct   4860
ctagaactag tggatccccc ggg                                            4883
```

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: primer 5TOPF

<400> SEQUENCE: 22

```
cagcaccatc agggctggca gcatagtaca tttcatctga c                          41
```

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: primer
      SCG8120R:

<400> SEQUENCE: 23
cgttgtggct gttgtagttg tac                                             23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer
      SCR728F

<400> SEQUENCE: 24
tgcggcggat ttatcttgca ag                                              22

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: primer
      5TOPR:

<400> SEQUENCE: 25
cagccctgat ggtgctggac tatttaggac caccgtagag                           40

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: primer
      SCR7320F

<400> SEQUENCE: 26
atatatgcgt gccgcgtggc ggatcccc                                        28

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer
      SCRG7672R

<400> SEQUENCE: 27
atatatcatg gtggctcgag ggtggtgtt                                       29

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: primer TOPF

<400> SEQUENCE: 28
caccatcagg gactacagca tagtacattt catctgac                             38

```
<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: primer TOPR

<400> SEQUENCE: 29
tagtccctga tggtgactat ttaggaccac cgtagag                                37
```